United States Patent
Collado Cano et al.

(10) Patent No.: US 7,125,871 B2
(45) Date of Patent: Oct. 24, 2006

(54) EXCITATORY AMINO ACID RECEPTOR MODULATORS

(75) Inventors: Ivan Collado Cano, Madrid (ES); Jesus Ezquerra-Carrera, Madrid (ES); Alicia Marcos Liorente, Madrid (ES); Luisa Maria Martin-Cabrejas, Madrid (ES); James Allen Monn, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 693 days.

(21) Appl. No.: 10/275,928

(22) PCT Filed: May 24, 2001

(86) PCT No.: PCT/US01/10831

§ 371 (c)(1),
(2), (4) Date: Jun. 6, 2003

(87) PCT Pub. No.: WO01/92212

PCT Pub. Date: Dec. 6, 2001

(65) Prior Publication Data

US 2004/0092553 A1    May 13, 2004

(30) Foreign Application Priority Data

May 31, 2000 (EP) .................. 00500110

(51) Int. Cl.
| | |
|---|---|
| A61K 31/535 | (2006.01) |
| A61K 31/47 | (2006.01) |
| A61K 31/44 | (2006.01) |
| C07D 265/30 | (2006.01) |
| C07D 217/06 | (2006.01) |
| C07D 213/62 | (2006.01) |
| C07D 233/40 | (2006.01) |

(52) U.S. Cl. .................. 514/237.5; 514/307; 514/355; 544/176; 546/146; 546/298; 548/317.1

(58) Field of Classification Search ............. 514/237.5, 514/307, 355; 544/176; 546/146, 298; 548/317.1
See application file for complete search history.

(56) References Cited

U.S. PATENT DOCUMENTS

| 6,172,058 B1 | 1/2001 | Pedregal-Terero et al. |
| 6,498,180 B1 | 12/2002 | Collado et al. |
| 6,504,052 B1 | 1/2003 | Collado et al. |

FOREIGN PATENT DOCUMENTS

| WO | 0 870 760 A | 10/1998 |
| WO | WO 01/92213 A2 | 12/2001 |

OTHER PUBLICATIONS

Pellicciari et al. "Synthesis and Pharmacological Characterization of All Sixteen Stereoisomers of 2-(2'-Carboxy-3'-phenylcyclopropyl)glycine. Focus on (2S,1'S,2'S,3'R)-2-(2'-Carboxy-3'-phenylcyclopropyl)glycine, a Novel and Selective Group II Metabotropic Glutamate Receptors Antagonist" J. Med. Chem. 1996, vol. 39, pp. 2259-2269.*

Pellicciari et al: "Synthesis and Pharmacological Characterization of All Sixteen Stereoisomers of 2-(2'-Carboxy-3'-phenylcyclopropyl)glycine. Focus on (2S.1'S.2'S.3'R)-2-(2'-Carboxy-3'-phenylcy clopropyl)glycine. a Novel and Selective Group II Metabotropic Glutamate Receptor Antagonist" Journal of Medicinal Chemistry. American Chemical Society. Washington. US. vol. 39. No. 11. 1996. pp. 2259-2269, XP002122695 ISSN: 0022-2623 cited in the application pp. 2259-2269.

* cited by examiner

Primary Examiner—Kamal A. Saeed
Assistant Examiner—Joseph R. Kosack
(74) Attorney, Agent, or Firm—Arvie J. Anderson

(57) ABSTRACT

Compounds of the formula (I) in which $R^1$, $R^2$ and $X^1$ have the meanings given in the specification, modulate metabotropic glutamate receptor function and are useful in treating disorders of the central nervous system

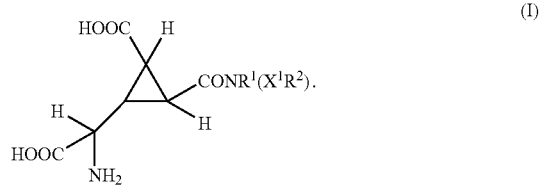

10 Claims, No Drawings

EXCITATORY AMINO ACID RECEPTOR MODULATORS

This application is a U.S. national phase entry, prudent to 35 USC 371, of PCT/US01/10831, filed May 24, 2001 and published on Dec. 6, 2001, International Publication No. WO 01/92212, which claims the benefit of European Application No. 00500110.2 filed May 31, 2000.

In the mammalian central nervous system (CNS), the transmission of nerve impulses is controlled by the interaction between a neurotransmitter, that is released by a sending neuron, and a surface receptor on a receiving neuron, which causes excitation of this receiving neuron. L-Glutamate, which is the most abundant neurotransmitter in the CNS, mediates the major excitatory pathway in mammals, and is referred to as an excitatory amino acid (EAA). The receptors that respond to glutamate are called excitatory amino acid receptors (EAA receptors). See Watkins & Evans, *Ann. Rev. Pharmacol. Toxicol.*, 21, 165 (1981); Monaghan, Bridges, and Cotman, *Ann. Rev. Pharmacol. Toxicol.*, 29, 365 (1989); Watkins, Krogsgaard-Larsen, and Honore, *Trans. Pharm. Sci.*, 11, 25 (1990). The excitatory amino acids are of great physiological importance, playing a role in a variety of physiological processes, such as long-term potentiation (learning and memory), the development of synaptic plasticity, motor control, respiration, cardiovascular regulation, and sensory perception.

Excitatory amino acid receptors are classified into two general types. Receptors that are directly coupled to the opening of cation channels in the cell membrane of the neurons are termed "ionotropic". This type of receptor has been subdivided into at least three subtypes, which are defined by the depolarizing actions of the selective agonists N-methyl-D-aspartate (NMDA), alpha-amino-3-hydroxy-5-methylisoxazole-4-propionic acid (AMPA), and kainic acid (KA). The second general type of receptor is the G-protein or second messenger-linked "metabotropic" excitatory amino acid receptor. This second type is coupled to multiple second messenger systems that lead to enhanced phosphoinositide hydrolysis, activation of phospholipase D or C, increases or decreases in c-AMP formation, and changes in ion channel function. Schoepp and Conn, *Trends in Pharmacol. Sci.*, 14, 13 (1993). Both types of receptors appear not only to mediate normal synaptic transmission along excitatory pathways, but also participate in the modification of synaptic connections during development and throughout life. Schoepp, Bockaert, and Sladeczek, *Trends in Pharmacol. Sci.*, 11, 508 (1990); McDonald and Johnson, *Brain Research Reviews*, 15, 41 (1990).

The excessive or inappropriate stimulation of excitatory amino acid receptors leads to neuronal cell damage or loss by way of a mechanism known as excitotoxicity. This process has been suggested to mediate neuronal degeneration in a variety of conditions. The medical consequences of such neuronal degeneration makes the abatement of these degenerative neurological processes an important therapeutic goal.

The metabotropic glutamate receptors are a highly heterogeneous family of glutamate receptors that are linked to multiple second-messenger pathways. These receptors function to modulate the presynaptic release of glutamate, and the postsynaptic sensitivity of the neuronal cell to glutamate excitation. Compounds which modulate the function of these receptors, in particular agonists and antagonists of glutamate, are useful for the treatment of acute and chronic neurodegenerative conditions, and as antipsychotic, anticonvulsant, analgesic, anxiolytic, antidepressant, and antiemetic agents.

Pellicciari et al., J. Med. Chem., 1996, 39, 2259–2269 refers to compounds known as metabotropic glutamate receptor agonists, in particular (2S, 1'S, 2'S)-2-(2-carboxycyclopropyl)glycine, also known as L-CCG-I; (2S, 1'S, 2'R, 3'R)-2-(2'-carboxy-3'-(methoxymethyl)cyclopropyl-glycine, also known as cis-MCG-I; (2S, 1'S, 2'R, 3'S)-2-(2'-carboxy-3'-(methoxymethyl)cyclopropylglycine, also known as trans-MCG-I; and (2S, 1'R, 2'R, 3'R)-2-(2',3'-dicarboxycyclopropyl)glycine, also known as DCG-IV. The paper also describes the synthesis of the sixteen possible stereoisomers of 2-(2'-carboxy-3'-phenylcyclopropyl)glycine and their evaluation as excitatory amino acid receptor ligands. The compound (2S, 1'S, 2'S, 3'R)-2-(2'-carboxy-3'-phenylcyclopropyl)glycine, also known as PCCG 4 is reported to be a metabotropic glutamate receptor antagonist.

Japanese patent application publication number JP 06179643 discloses MCG and generically discloses (2S, 1'S, 2'R)-2-(2-carboxy-3-alkoxymethyl- and 3-aralkoxymethylcyclopropyl)glycines as glutamate receptor agonists.

International patent application publication number WO 97/19049 discloses PCCG 4 and also generically discloses various 2-carboxy-3-arylcyclopropylglycines having affinity for metabotropic glutamate receptors.

International patent application publication number WO 98/00391 discloses 2-carboxy-3,3-dihalocyclopropylglycines, including (2S, 1'S, 2'S)-2-(2-carboxy-3,3-difluoro)-cyclopropylglycine as metabotropic glutamate receptor agonists.

European patent application, publication number EP-A1-0870760 discloses that certain 3-substituted 2-carboxycyclopropyl glycine derivatives are modulators of metabotropic glutamate receptor function. The preferred compounds are said to be those in which the substituents at the 1 and 2 positions are in a trans relationship. The examples illustrate such compounds in which the substituents at the 1 and 3 positions are also in a trans relationship. One such compound is (2S, 1'S, 2'S, 3'S)-2'-carboxy-3'-methylcyclopropylglycine.

Dawei Ma et al., Org. Lett. (1999), 1(2), 285–287 discloses a synthesis of (2S, 1'R, 2'R, 3'R)-2-(2',3'-dicarboxypropyl)glycine (L-DCG-IV). In the final step of the synthesis, the compound (2S, 1'S, 2'R, 3'R)-N-(tert-butoxycarbonyl)-2-[2'-methoxycarbonyl-3'-diethylaminocarbonyl)cyclopropyl]glycine is hydrolyzed in the presence of hydrochloric acid.

Surprisingly, novel 3-substituted 2-carboxycyclopropyl glycine derivatives have now been found which are potent agonists of glutamate at metabotropic glutamate receptors.

Accordingly, the present invention provides a compound of the formula:

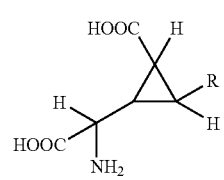

I in which:

R represents CN, 1H-tetrazol-5-yl or a group of formula CONR¹(X¹R²);

$X^1$ represents a bond, NHCO, NH, O or $(CH_2)_p$—Y— in which Y represents O, S, $NR^b$, or COO and p is 2 or 3, and $R^1$, $R^2$ and
$R^b$ each independently represents hydrogen; $C_{1-10}$ alkyl; $C_{2-10}$ alkenyl; $C_{2-10}$ alkynyl; aryl; aryl-$C_{1-10}$ alkyl; aryl-$C_{2-10}$ alkenyl; aryl-$C_{2-10}$ alkynyl; heteroaryl; $C_{3-8}$ cycloalkyl; $C_{3-8}$-cycloalkyl-$C_{1-10}$ alkyl; a group of formula $CH(R^3)$COOH in which $R^3$ represents an amino acid residue; or
$R^1$ and $X^1R^2$ together with the nitrogen atom to which they are attached form a 5 to 6-membered saturated heterocyclic ring, which ring may optionally be fused with an aromatic ring;
an ester thereof;
or a salt of said compound of formula I or said ester thereof.

Compounds of the invention have been found to be agonists of glutamate at metabotropic glutamate receptors and are therefore useful in the treatment of diseases of the central nervous system such as neurological diseases, for example neurodegenerative diseases, and as antipsychotic, anxiolytic, drug-withdrawal, antidepressant, anticonvulsant, analgesic and anti-emetic agents.

It will be appreciated that the compounds of formula (I) contain at least four asymmetric carbon atoms, three being in the cyclopropane ring and one being at the α-carbon of the amino acid group. Accordingly, the compounds of the invention may exist in and be isolated in enantiomerically pure form, in racemic form, or in a diastereoisomeric mixture.

Preferred compounds of the invention are those of formula Ia

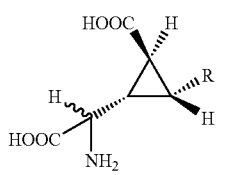

Ia

The amino acid moiety preferably has the natural amino configuration. Accordingly, preferred compounds according to the invention are those of the formula:

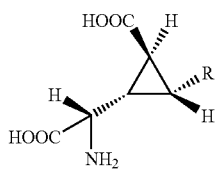

Ib

As used herein, the terms alkyl, alkenyl and alkynyl refer to straight chain or branched groups.

The term $C_{1-10}$ alkyl includes $C_{1-8}$ alkyl, $C_{1-6}$ alkyl and $C_{1-4}$ alkyl. Particular values are methyl, ethyl, propyl, isopropyl, butyl, isobutyl, t-butyl, pentyl, hexyl, heptyl, octyl, nonyl and decyl.

The term $C_{2-10}$ alkenyl includes $C_{3-10}$ alkenyl. Particular values are vinyl and prop-2-enyl. The term also includes groups containing more than one double bond, for example alkadienyl groups, such as 1,3-butadienyl.

The term $C_{2-10}$ alkynyl includes $C_{3-10}$ alkynyl. A particular value is prop-2-ynyl. The term also includes groups containing more than one triple bond, or one or more double bonds.

The term aryl group, as such or in an aryl-$C_{1-10}$ alkyl, aryl-$C_{2-10}$ alkenyl or aryl-$C_{2-10}$ alkynyl group, refers to an aromatic monocyclic or polycyclic carbocyclic ring that may be unsubstituted or substituted by one or more substituents, said substituents being selected from atoms and groups that, when present in the compound of formula I, do not prevent the compound of formula I from functioning as a metabotropic glutamate receptor agonist.

Examples of an aromatic monocyclic or polycyclic carbocyclic ring in an aryl group include phenyl and naphthyl.

An aromatic monocyclic or polycyclic carbocyclic ring in an aryl group may be unsubstituted or substituted with, for example, one, two or three substituents selected independently from halogen, cyano, nitro, amino, (1–4C)alkylamino, di(1–4C)alkylamino, carboxy, and a group of formula —$(CH_2)_m$—$X^a$—$(CH_2)_n$—$R^a$ in which m is 0, 1 or 2, n is 0, 1 or 2, $X^a$ represents a bond, O, S, SO, $SO_2$, NH, CO, COO, OCO, CONH, NHCO, NHCONH, $NHSO_2$ or $SO_2NH$ and $R^a$ represents an $C_{1-4}$ alkyl, $C_{2-4}$ alkenyl, $C_{2-4}$ alkynyl, halo $C_{1-4}$ alkyl or phenyl group which is unsubstituted or substituted by one or two substituents selected independently from halogen, (1–4C)alkyl and (1–4C)alkoxy.

An example of a particular value for an aryl group is phenyl.

The term heteroaryl refers to an aromatic 5–6 membered ring containing from one to four heteroatoms selected from oxygen, sulfur and nitrogen, and a bicyclic group consisting of a 5–6 membered ring containing from one to four heteroatoms selected from oxygen, sulfur and nitrogen fused with a benzene ring or a 5–6 membered ring containing from one to four heteroatoms selected from oxygen, sulfur and nitrogen. Examples of heteroaromatic groups are furyl, thiophenyl, oxazolyl, isoxazolyl, thiazoyl, isothiazolyl, imidazolyl, pyrimidyl, benzofuryl, benzothiophenyl, benzimidazolyl, benzoxazolyl, benzo-thiazolyl and indolyl.

The term $C_{3-8}$ cycloalkyl, as such or in the term $C_{3-8}$ cycloalkyl-$C_{1-10}$ alkyl, includes monocyclic and polycyclic groups. It includes $C_{3-6}$ cycloalkyl. Examples of particular values are cyclopropyl, cyclobutyl, cyclopentyl, cyclohexyl and bicyclo[2.2.2]octane.

The term halogen includes fluorine, chlorine, bromine and iodine.

The term amino acid residue refers to a group that is bonded to the alpha-carbon atom in an amino acid (the carbon also bearing an amino and carboxyl group) in an amino acid selected from D and L:

| | |
|---|---|
| Ala | Alanine |
| Arg | Arginine |
| Asn | Asparagine |
| Asp | Aspartic acid |
| Cys | Cysteine |
| Gln | Glutamine |
| Glu | Glutamic acid |
| Gly | Glycine |
| His | Histidine |
| Ile | Isoleucine |
| Leu | Leucine |

| | -continued |
|---|---|
| Lys | Lysine |
| Met | Methionine |
| Phe | Phenylalanine |
| Pro | Proline |
| Ser | Serine |
| Thr | Threonine |
| Trp | Tryptophan |
| Try | Tyrosine |
| Val | Valine |

An example of a preferred value for an amino acid residue is hydrogen (Gly).

The term a 5 to 6-membered saturated heterocyclic ring, which ring may optionally be fused with an aromatic ring refers to a 5- or 6-membered saturated ring that may contain, in addition to the nitrogen atom bearing $R^1$ and $X^1R^2$ a second heteroatom selected from O, N and S, which ring may be fused with an aromatic ring. Examples of 5- and 6-membered saturated rings are piperidinyl and morpholinyl. An example of an aromatic ring is phenyl.

Examples of particular values for a 5 to 6-membered saturated heterocyclic ring, which ring may optionally be fused with an aromatic ring include morpholinyl and tetrahydroisoquinolinyl.

Examples of particular values for $R^1$ are hydrogen and methyl.

Especially preferred are compounds in which $R^1$ is hydrogen.

Examples of particular values for $R^2$ are:

hydrogen;
for $C_{1-10}$ alkyl: methyl;
for $C_{2-10}$ alkenyl: allyl;
for $C_{2-10}$ alkynyl: propargyl;
for aryl: phenyl;
for heteroaryl: pyridyl;
for aryl-$C_{1-10}$ alkyl: benzyl;
for aryl-$C_{2-10}$ alkenyl: cinnamyl;
for aryl-$C_{2-10}$ alkynyl: phenylethynyl;
for $C_{3-8}$ cycloalkyl: cyclopentyl;
for $C_{3-8}$-cycloalkyl-$C_{1-10}$ alkyl: cyclohexylmethyl
for a group of formula $CH(R^3)COOH$: $CH_2COOH$; and
for a group that together with $X^1$, $R^1$ and the nitrogen to which they are attached forms a 5 to 6-membered saturated heterocyclic ring, which ring may optionally be fused with an aromatic ring: morpholinyl and tetrahydroisoquinolinyl.

Examples of particular values for $R^2X^1$ are hydrogen; methyl; phenyl; benzyl; cyclohexyl; cyclohexylmethyl, $HOOCCH_2$; phenyl$CONH$ and, together with $R^1$ and the nitrogen to which they are attached, morpholinyl and tetrahydroisoquinolinyl.

Particularly preferred compounds are:
(2SR, 1'SR, 2'RS, 3'RS)-2-[2'-carboxy-3'-(phenylmethylaminocarbonyl)cyclopropyl]glycine;
(2SR, 1'SR, 2'RS, 3'RS)-2-[2'-carboxy-3'-(methylaminocarbonyl)cyclopropyl]glycine;
(2SR, 1'SR, 2'RS, 3'RS)-2-[2'-carboxy-3'-(cyclohexylmethylaminocarbonyl)cyclopropyl]glycine;
(2SR, 1'SR, 2'RS, 3'RS)-2-[3'-(benzoylhydrazinocarbonyl)-2'-carboxycyclopropyl]glycine;
(2SR, 1'SR, 2'RS, 3'RS)-2-[2'-carboxy-3'-(carboxymethylaminocarbonyl)cyclopropyl]glycine;
(2SR, 1'SR, 2'RS, 3'RS)-2-[2'-carboxy-3'-(phenylaminocarbonyl)cyclopropyl]glycine;
(2SR, 1'SR, 2'RS, 3'RS)-2-[2'-carboxy-3'-(dimethylaminocarbonyl)cyclopropyl]glycine;
(2SR, 1'SR, 2'RS, 3'RS)-2-[2'-carboxy-3'-(morpholinylcarbonyl)cyclopropyl]glycine;
(2SR, 1'SR, 2'RS, 3'RS)-2-[2'-carboxy-3'-(tetrahydroisoquinolylcarbonyl)cyclopropyl]glycine;
(2SR, 1'SR, 2'RS, 3'RS)-2-[2'-carboxy-3'-(phenylhydrazinocarbonyl)cyclopropyl]glycine hydrochloride;
(2SR, 1'SR, 2'RS, 3'RS)-2-[2'-carboxy-3'-(3"-pyridylcarbonylhydrazinocarbonyl)cyclopropyl]glycine;
(2SR, 1'SR, 2'RS, 3'RS)-2-[2'-carboxy-3'-(3"-methoxybenzoylhydrazinocarbonyl)cyclopropyl]glycine;
(2SR, 1'SR, 2'RS, 3'RS)-2-[2'-carboxy-3'-(2"-phenylethylaminocarbonyl)cyclopropyl]glycine;
(2SR, 1'SR, 2'RS, 3'RS)-2-[2'-carboxy-3'-(benzyloxiaminocarbonyl)cyclopropyl]glycine;
(2SR, 1'SR, 2'RS, 3'RS)-2-[2'-carboxy-3'-(3"methoxypropylaminocarbonyl)cyclopropyl]glycine;
(2SR, 1'SR, 2'RS, 3'RS)-2-[2'-carboxy-3'-(2"dimethylaminoethylaminocarbonyl)cyclopropyl]glycine;
(2SR, 1'SR, 2'RS, 3'RS)-2-[2'-carboxy-3'-cyanocyclopropyl]glycine; and
(2SR, 1'SR, 2'RS, 3'RS)-2-[2'-carboxy-3'-(tetrazol-5'-yl)cyclopropyl]glycine;
and pharmaceutically acceptable salts and esters thereof.

The present invention includes salts of the formula (I) compounds. These salts can exist in conjunction with the acidic or basic portion of the molecule and can exist as acid addition, primary, secondary, tertiary, or quaternary ammonium, alkali metal, or alkaline earth metal salts. Generally, the acid addition salts are prepared by the reaction of an acid with a compound of formula (I). The alkali metal and alkaline earth metal salts are generally prepared by the reaction of the hydroxide form of the desired metal salt with a compound of formula (I).

The salts of the compounds of formula I may be pharmaceutically-acceptable salts. However, other salts are included in the invention. They may serve as intermediates in the purification of compounds or in the preparation of other, for example pharmaceutically-acceptable, acid addition salts, or are useful for identification, characterisation or purification.

Acid addition salts are preferably the pharmaceutically acceptable, non-toxic addition salts with suitable acids, such as those with inorganic acids, for example hydrochloric, hydrobromic, nitric, sulphuric or phosphoric acids, or with organic acids, such as organic carboxylic acids, for example, glycollic, maleic, hydroxymaleic, fumaric, malic, tartaric, citric, salicyclic, o-acetoxybenzoic, or organic sulphonic, 2-hydroxyethane sulphonic, toluene-p-sulphonic, or naphthalene-2-sulphonic acid.

The present invention includes esters of the formula (I) compounds.

The esters of the compounds of formula I may be pharmaceutically acceptable metabolically labile esters of compounds of formula I. These are ester derivatives of compounds of formula I that are hydrolyzed in vivo to afford said compound of formula I and a pharmaceutically acceptable alcohol. Examples of metabolically labile esters include esters formed with (1–6C) alkanols in which the alkanol moiety may be optionally substituted by a (1–8C) alkoxy group, for example methanol, ethanol, propanol and methoxyethanol. The most preferred esters are alkyl esters derived from $C_{1-4}$ alkanols, especially methyl and ethyl esters.

The present invention also includes esters of compounds of formula I other than pharmaceutically acceptable metabolically labile esters. Such esters are useful as intermediates in the preparation of compounds of formula I.

According to another aspect, the present invention also provides a process for preparing a compound of formula I, an ester thereof or a salt of said compound of formula I or said ester thereof, which comprises:

(a) deprotecting a compound of formula

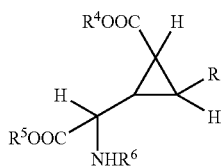

II in which $R^4$ and $R^5$ each independently represents hydrogen or a carboxyl protecting group, and $R^6$ represents hydrogen or an amine protecting group;

(b) hydrolysing a compound of formula

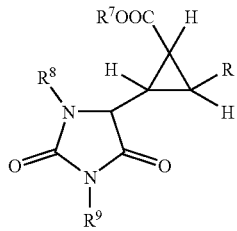

III in which $R^7$ represents a hydrogen atom or a carboxyl protecting group, and $R^8$ and $R^9$ each independently represents a hydrogen atom, a $C_{1-4}$ alkyl group or a phenyl $C_{1-4}$ alkyl group in which the phenyl group is unsubstituted or substituted by halo, $C_{1-4}$ alkyl, $C_{1-4}$ alkoxy or $C_{3-4}$ alkenyl; or (c) hydrolysing a compound of formula

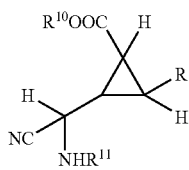

IV in which $R^{10}$ represents a hydrogen atom or a carboxy protecting group, and $R^{11}$ represents a hydrogen atom or an amine protecting group;

followed when necessary by recovering a diastereomer or isomer of the compound, or forming an ester thereof or a salt of said compound of formula I or said ester thereof.

The protection of carboxylic acid groups is described in McOmie, Protecting Groups in Organic Chemistry, Plenum Press, NY, 1973, and Greene and Wuts, Protecting Groups in Organic Synthesis, 2nd. Ed., John Wiley & Sons, NY, 1991. Examples of carboxy protecting groups include $C_1$–$C_6$ alkyl groups such as methyl, ethyl, t-butyl and t-amyl; aryl ($C_1$–$C_4$)alkyl groups such as benzyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, benzhydryl and trityl; silyl groups such as trimethylsilyl and t-butyldimethylsilyl; and allyl groups such as allyl and 1-(trimethylsilylmethyl)prop-1-en-3-yl.

Examples of amine protecting groups include acyl groups, such as groups of formula $R^{12}CO$ in which $R^{12}$ represents $C_{1-6}$ alkyl, $C_{3-10}$ cycloalkyl, phenyl $C_{1-6}$ alkyl, phenyl, $C_{1-6}$ alkoxy, phenyl $C_{3-6}$ alkoxy, or a $C_{3-10}$ cycloalkoxy, wherein a phenyl group may be optionally substituted, for example by one or two of halogen, $C_1$–$C_4$ alkyl and $C_1$–$C_4$ alkoxy. Preferred amino protecting groups include t-butoxycarbonyl (Boc) and benzyl.

Examples of particular values for $R^4$, $R^5$, $R^7$ and $R^{10}$ are hydrogen, methyl, ethyl, n-propyl, n-butyl, t-butyl, benzyl, 4-methoxybenzyl, phenylethyl and phenylpropyl.

Examples of particular values for $R^6$ and $R^{11}$ include acetyl and tert-butoxycarbonyl.

Examples of particular values for $R^8$ and $R^9$ are hydrogen and benzyl.

The compounds of formula (II) may be deprotected by conventional methods. Thus, an alkyl carboxyl protecting group may be removed by hydrolysis. The hydrolysis may conveniently be performed by heating the compound of formula (II) in the presence of either a base, for example an alkali metal hydroxide such as lithium, sodium or potassium hydroxide, or an alkaline metal hydroxide, such as barium hydroxide, or an acid such as hydrochloric acid. The hydrolysis is conveniently performed at a temperature in the range of from 0° C. to 100° C. Convenient reaction media include aqueous solvents, such as aqueous tetrahydrofuran. An aralkyl carboxyl protecting group may conveniently be removed by hydrogenation. The hydrogenation may be effected by reacting the compound of formula (II) with hydrogen in the presence of a Group VIII metal catalyst, for example a palladium catalyst such as palladium on charcoal. Suitable solvents for the reaction include alcohols such as ethanol. The reaction is conveniently performed at a temperature in the range of from 0° C. to 100° C.

An acyl, amine protecting group is also conveniently removed by hydrolysis, for example as described for the removal of an alkyl carboxyl protecting group. Thus, a tert-butoxycarbonyl, amine protecting group may conveniently be removed in the presence of a base, for example an alkali metal hydroxide such as lithium, sodium or potassium hydroxide, or an alkaline metal hydroxide, such as barium hydroxide or an acid such as hydrochloric acid. The hydrolysis is performed in the presence of an aqueous solvent, such as aqueous tetrahydrofuran, at a temperature in the range of from 0° C. to 100° C.

It will be appreciated that the protecting groups and reaction conditions should be selected so as not to affect any other functional group in the molecule, such as the group $CONR^1(X^1R^2)$.

The compounds of formula III are conveniently hydrolyzed in the presence of a base, for example an alkali metal hydroxide such as lithium, sodium or potassium hydroxide, or an alkaline earth metal hydroxide such as barium hydroxide. Suitable reaction media include water. The temperature is conveniently in the range of from 0° C. to 100° C. It will be appreciated that the reaction conditions should be selected so as not to affect the group $CONR^1(X^1R^2)$.

The compounds of formula IV are conveniently hydrolyzed in the presence of an acid, such as hydrochloric acid or sulfuric acid, or a base, such as an alkali metal hydroxide, for example sodium hydroxide. The hydrolysis is conveniently performed in an aqueous solvent such as water, or in an alkanol such as methanol or ethanol, and at a temperature in the range of from 0° C. to 100° C. It will be appreciated that the reaction conditions should be selected so as not to affect the group $CONR^1(X^1R^2)$.

Compounds of formula I in the form of diastereomeric mixtures or isomers may be obtained in a conventional manner, for example by chiral synthesis using chiral starting materials, of by using conventional separation techniques, for example by forming a crystalline salt with a chiral acid or base.

Compounds of formula (II) in which R represents $CONR^1(X^1R^2)$ may be prepared by reacting a compound of formula (V)

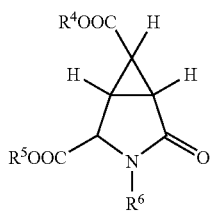

with an amine of formula (VI)

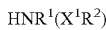

According to one method, the reaction is performed in the presence of an alkali metal cyanide, such as potassium cyanide, under irradiation with ultrasound. Convenient solvents include ethers, such as tetrahydrofuran. The reaction is conveniently effected at a temperature of from 0 to 100° C.

According to another method, the reaction is performed in the presence of a Lewis acid, such as aluminium trichloride. Convenient solvents include halogenated hydrocarbons, such as dichloromethane. The reaction is conveniently effected at a temperature of from 0 to 100° C.

According to yet another method, a compound of formula V may be reacted with ammonia in the presence of trimethylaluminium to afford a compound of formula I in which R is $CONH_2$.

Compounds of formula II in which R represents cyano may be prepared by dehydrating a corresponding compound of formula II in which R represents $CONH_2$. The reaction is conveniently performed in the presence of a dehydrating agent, such as trifluoroacetic acid anhydride or thionyl chloride, and in the presence of a base such as pyridine. Convenient solvents include ethers such as tetrahydrofuran. The reaction is conveniently effected at a temperature of from 0 to 100° C.

Compounds of formula II in which R represents 1H-tetrazol-5-yl may be prepared by reacting a corresponding compound of formula II in which R represents CN with an alkali metal azide, such as sodium azide, or $Bu_3SnN_3$, or $TMS-N_3$. The reaction is conveniently effected at temperature of from 0 to 150° C. Convenient solvents include ethers, such as tetrahydrofuran or dioxane, and aprotic solvents such as toluene.

The compounds of formula V may be prepared by oxidising a compound of formula

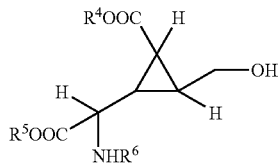

The oxidation is conveniently effected by reaction with an oxidising agent, such as Jones reagent (a solution of $Na_2Cr_2O_7.2H_2O$ in sulfuric acid). Convenient solvents include ketones, such as acetone. The reaction is conveniently effected at a temperature of from −25 to 10° C.

The compounds of formula VII may be prepared by hydrolysing a compound of formula VIII

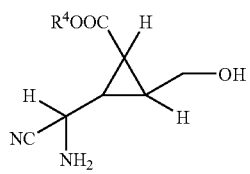

followed by introducing the protecting group $R^6$. The hydrolysis is conveniently performed in the presence of an acid, such as hydrochloric acid. Suitable solvents include aqueous alcohols, such as aqueous ethanol. A t-butoxycarbonyl protecting group may be introduced by reaction with di-tert-butyldicarbonate in the presence of sodium bicarbonate and in a reaction medium such as tetrahydrofuran or dioxan.

Alternatively, the compounds of formula VII may be prepared by hydrolysing a compound of formula IX

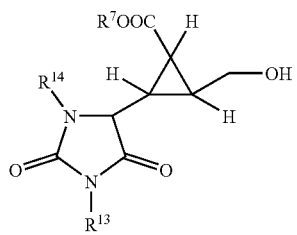

in which $R^{13}$ and $R^{14}$ are as defined for $R^8$ and $R^9$ followed by introducing the carboxyl protecting groups $R^4$ and $R^5$ and the amino protecting group $R^6$. The hydrolysis is conveniently performed in the presence of a base, such as sodium hydroxide, in an aqueous reaction medium, such as water. Alkyl carboxyl protecting groups may be introduced by reaction with the appropriate alkanol, for example ethanol, in the presence of an acid, such as hydrochloric acid. A t-butoxycarbonyl protecting group may be introduced by reaction with di-tert-butyldicarbonate in the presence of sodium bicarbonate and in a reaction medium such as tetrahydrofuran or dioxan.

The compounds of formula VIII may be prepared by reacting a compound of formula X

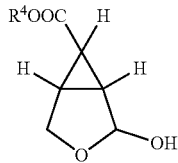

X with ammonium chloride and potassium cyanide in the presence of aluminium oxide. A convenient solvent is acetonitrile.

The compounds of formula IX may be prepared by hydrolysing a compound of formula X with an alkali metal hydroxide, for example using sodium hydroxide in aqueous ethanol, followed by treatment with an alkali metal cyanide, such as lithium, sodium or potassium cyanide, and ammonium carbonate in an aqueous alcohol, such as aqueous ethanol. Conveniently the reaction is performed at a temperature of from 35° C. to 150° C.

The compounds of formula X may be prepared by oxidising a compound of formula XI

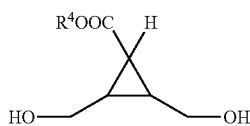

XI for example by employing a Swern oxidation.

The compounds of formula XI may be prepared by reacting a compound of formula XII

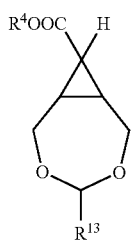

XII in which $R^{13}$ represents a hydrogen atom, a $C_{1-4}$ alkyl group or a phenyl group, with HCl or camphorsulfonic acid in an alkanol such as ethanol.

The compounds of formula XII may be prepared by reacting a compound of formula XIII

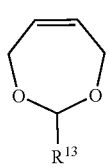

XIII with a compound of formula $$N_2CHCOOR^4 \qquad\qquad XIV$$

in the presence of $Rh_2(OAc)_4$. A convenient solvent is pentane.

The compounds of formula III in which R represents $CONR^1(X^1R^2)$ may be prepared by reacting a compound of formula

XV with an alkali metal cyanide, such as lithium, sodium or potassium cyanide, and ammonium carbonate in an aqueous alcohol, such as aqueous ethanol. Conveniently the reaction is performed at a temperature of from 35° C. to 150° C. If desired, the compounds of formula (III) may then be alkylated, for example using a compound of formula $R^8Cl$ or $R^9Cl$. The alkylated compounds are readily separated into their diastereomers.

Compounds of formula IV in which R represents $CONR^1(X^1R^2)$ may be prepared by reacting a compound of formula XV with an alkali metal cyanide, such as lithium, sodium or potassium cyanide, and an ammonium halide, such as ammonium chloride. The reaction is advantageously performed in the presence of ultrasound. Thus, the ammonium halide and alkali metal cyanide are advantageously mixed with chromatography grade alumina in the presence of a suitable diluent, such as acetonitrile. The mixture is then irradiated with ultrasound, whereafter the compound of formula XV is added, and the mixture is again irradiated.

The resultant mixture of diastereoisomeric aminonitriles may then be reacted with an acylating agent, such as acetyl chloride in the presence of a suitable base, for example an amine such as diisopropylamine, and in the presence of a suitable solvent such as dichloromethane, to afford a mixture of diastereomeric acylaminonitriles. The desired stereoisomer may conveniently be separated from this mixture, for example by chromatography.

The compounds of formula XV may be prepared by oxidising a compound of formula XI, for example by a Swern oxidation.

It will be appreciated that in order to obtain a compound of formula I which is in the configuration of formula Ib, the intermediates must be prepared in the appropriate configurations. The following formulae illustrate the respective configurations for each of the intermediates.

Ib

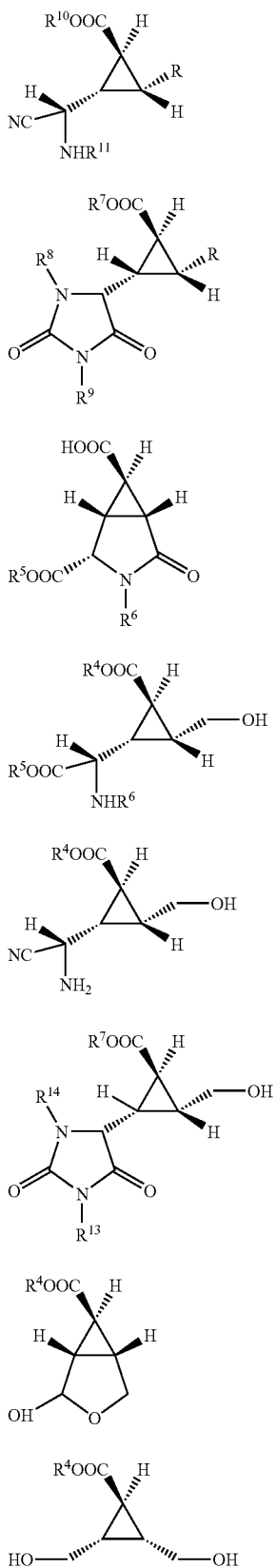

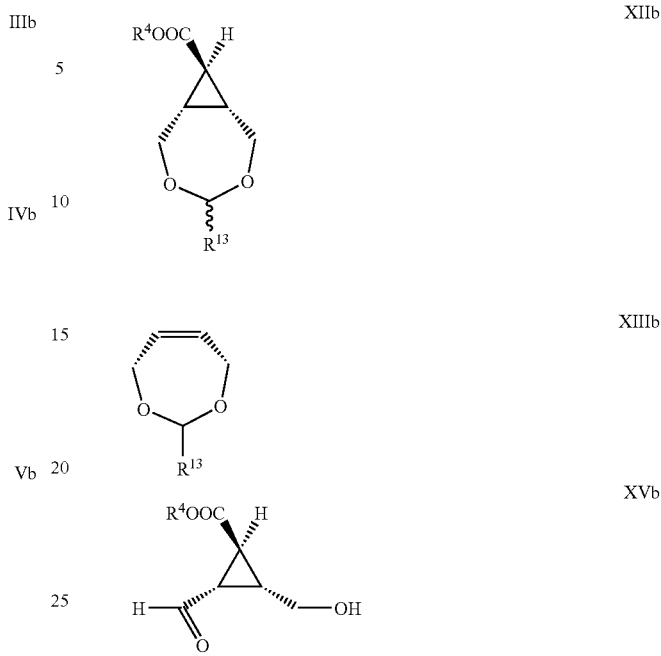

Many of the intermediates described herein are novel, and are therefore provided as further aspects of the invention.

As described hereinabove, the compounds of the invention are useful for the treatment of disorders of the central nervous system.

According to another aspect therefore, the present invention provides a method of treating a patient suffering from or susceptible to a disorder of the central nervous system, which comprises administering an effective amount of a compound of formula I as defined hereinabove, a pharmaceutically acceptable metabolically labile ester thereof or a pharmaceutically acceptable salt of said compound of formula I or said pharmaceutically acceptable metabolically labile ester thereof.

The particular effective amount or dose of compound administered according to this invention will of course be determined by the particular circumstances surrounding the case, including the compound administered, the route of administration, the particular condition being treated, and similar considerations. The compounds can be administered by a variety of routes including oral, rectal, transdermal, subcutaneous, intravenous, intramuscular, or intranasal routes. Alternatively, the compound may be administered by continuous infusion. A typical daily dose will contain from about 0.01 mg/kg to about 100 mg/kg of the active compound of this invention. Preferably, daily doses will be about 0.05 mg/kg to about 50 mg/kg, more preferably from about 0.1 mg/kg to about 25 mg/kg.

A variety of physiological functions have been shown to be subject to influence by excessive or inappropriate stimulation of excitatory amino acid transmission. The formula I compounds of the present invention are believed to have the ability to treat a variety of neurological disorders in patients associated with this condition, including acute neurological disorders such as cerebral deficits subsequent to cardiac bypass surgery and grafting, stroke, cerebral ischemia, spinal cord trauma, head trauma, perinatal hypoxia, cardiac arrest, and hypoglycemic neuronal damage. The formula I compounds are believed to have the ability to treat a variety of chronic neurological disorders, such as Alzheimer's disease, Huntington's Chorea, amyotrophic lateral sclerosis, AIDS-induced dementia, ocular damage and retinopathy, cognitive disorders, and idiopathic and drug-induced Parkinson's. The present invention also provides methods for treating these disorders which comprises administering to a patient in need thereof an effective amount of a compound of formula I or a pharmaceutically acceptable metabolically labile ester thereof, or a pharmaceutically acceptable salt thereof.

The formula I compounds of the present invention are also believed to have the ability to treat a variety of other neurological disorders in patients that are associated with glutamate dysfunction, including muscular spasms, convulsions, migraine headaches, urinary incontinence, psychosis, (such as schizophrenia), drug tolerance and withdrawal (such as nicotine, opiates and benzodiazepines), anxiety and related disorders, emesis, brain edema, chronic pain, and tardive dyskinesia. The formula I compounds are also useful as antidepressant and analgesic agents. Therefore, the present invention also provides methods for treating these disorders which comprise administering to a patient in need thereof an effective amount of the compound of formula I, or a pharmaceutically acceptable metabolically labile ester thereof, or a pharmaceutically acceptable salt thereof.

The term "treating" for purposes of the present invention, includes prophylaxis, amelioration or elimination of a named condition once the condition has been established.

The term "patient" for purposes of the present invention is defined as any warm blooded animal such as, but not limited to, a mouse, guinea pig, dog, horse, or human. Preferably, the patient is human.

According to another aspect, the present invention provides a compound of formula I as defined hereinabove, or a pharmaceutically acceptable metabolically labile ester thereof, or a pharmaceutically acceptable salt thereof, for use in therapy.

According to yet another aspect, the present invention provides the use of a compound of formula I as defined hereinabove, or a pharmaceutically acceptable metabolically labile ester thereof, or a pharmaceutically acceptable salt thereof, for the manufacture of a medicament for treating a disorder of the central nervous system.

The ability of compounds to modulate metabotropic glutamate receptor function may be demonstrated by examining their ability to influence either cAMP production (mGluR 2, 3, 4, 6, 7 or 8) or phosphoinositide hydrolysis (mGluR 1 or 5) in cells expressing these individual human metabotropic glutamate receptor (mGluR) subtypes. (D. D. Schoepp, et al., *Neuropharmacol.*, 1996, 35, 1661–1672 and 1997, 36, 111).

In these tests the compounds exemplified herein have all been found to reverse [3H] LY341495 binding with a Ki of less than 30,000 nM at =GluR2. For example, the compound of Example 1 of the present application was found to reverse [3H] LY341495 binding with a Ki of 3421 nM at mGluR2. (LY341495 is described in Ornstein et al., J. Med. Chem., 1998, 41, 346–357 and J. Med. Chem., 1998, 41, 358 to 378).

The compounds of the present invention are preferably formulated prior to administration. Therefore, another aspect of the present invention is a pharmaceutical formulation comprising a compound of formula I, a pharmaceutically acceptable metabolically labile ester thereof, or a pharmaceutically acceptable salt thereof, and a pharmaceutically-acceptable carrier, diluent, or excipient. The present pharmaceutical formulations are prepared by known procedures using well-known and readily available ingredients. In making the compositions of the present invention, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragacanth, gelatin, calcium silicate, microcrystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. Compositions of the invention may be formulated so as to provide quick, sustained, or delayed release of the active ingredient after administration to the patient by employing procedures well known in the art.

The compositions are preferably formulated in a unit dosage form, each dosage containing from about 5 mg to about 500 mg, more preferably about 25 mg to about 300 mg of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient. The following formulation examples are illustrative only and are not intended to limit the scope of the invention in any way.

Formulation 1

Hard gelatin capsules are prepared using the following ingredients:

|  | Quantity (mg/capsule) |
| --- | --- |
| Active Ingredient | 250 |
| Starch, dried | 200 |
| Magnesium stearate | 10 |
| Total | 460 mg |

The above ingredients are mixed and filled into hard gelatin capsules in 460 mg quantities.

Formulation 2

Tablets each containing 60 mg of active ingredient are made as follows:

| Active Ingredient | 60 mg |
| --- | --- |
| Starch | 45 mg |
| Microcrystalline cellulose | 35 mg |

-continued

| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

The following Examples illustrate the invention. In the Examples, the term $Et_2O$ signifies diethylether, AcOEt signifies ethyl acetate, EtOH signifies ethanol, $Et_3N$ signifies triethylamine, THF signifies tetrahydrofuran, $Bu_3SnN_3$ signifies tributyl tin azide, and Jones Reagent signifies a solution of 1.0 g of $Na_2Cr_2O_7.2H_2O$, and 1.34 g of sulfuric acid in $H_2O$ (total volume 5 mL).

Preparation 1

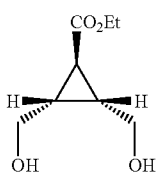

Ethyl 2,3-dihydroxyymethylcyclopropane carboxylate

To a solution of cis-4,7-dihydro-1,3-dioxepin (4.57 g, 45.6 mmol) in pentane (25 mL) under nitrogen at room temperature, $Rh_2(OAc)_4$ (220 mg, 0.5 mmol) was added. To the resulting suspension vigorously stirred, a solution of ethyl diazoacetate (10.5 mL, 100 mmol) in pentane (75 mL) was added dropwise at room temperature over a period of 3–4 hours. After the addition was completed, solvent was removed under vacuo and residue was chromatographed using a gradient of AcOEt/Hexane 1:10 to 1:5 as eluent. 6.75 g of an inseparable mixture of cyclopropanated product and $EtO_2CCH=CHCO_2Et$ was obtained. A solution of this mixture in ethanol saturated with hydrogen chloride (250 mL) was stirred overnight at room temperature. The following day, solvent was removed under vacuo and residue taken into ethanol (100 mL). This solution was neutralized with $NaHCO_3$ (solid), filtered and concentrated. The resulting residue was chromatographed using a gradient of AcOEt/Hexane 1:1 to 3:1 as eluent to give 4.3 g (56% yield) of diol.

$^1$H-NMR (200 MHz, $CDCl_3$): 1.23 (t, J=7.1 Hz, 3H), 1.49 (t, J=3.5, 1H), 1.89–2.00 (m, 2H), 2.72 (br s, 2H), 3.31–3.42 (m, 2H), 4.05–4.16 (m, 2H) and 4.10 ppm (c, J=7.1 Hz, 2H).

$^{13}$C-NMR (50 MHz, $CDCl_3$): 14.0, 23.8, 27.1 (2C), 60.3 (2C), 60.8 and 172.8 ppm.

Preparation 2

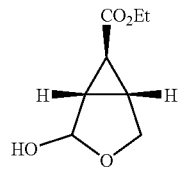

Ethyl (1RS, 5SR, 6RS)-2-hydroxy-3-oxabicyclo-[3.1.0] hexane-6-carboxylate

To a solution of oxalyl chloride (0.38 mL, 4.48 mmol) in $CH_2Cl_2$ (20 mL) at −78° C. under nitrogen atmosphere, dimethylsulfoxide (0.66 mL, 9.33 mmol) was added and stirred for 20 minutes. To this mixture, a solution of the product of Preparation 1 (650 mg, 3.73 mL) in $CH_2Cl_2$ was added and reaction was stirred at the same temperature for 30 minutes. Then, triethylamine (2.6 mL, 18.65 mmol) was added and the mixture was allowed to react at room temperature. After 30 minutes, the reaction mixture was quenched with water, the layers were separated and the aqueous layer was extracted with $CH_2Cl_2$ (2X). The combined organic layers were dried ($Na_2SO_4$), filtered and evaporated to give a residue which was chromatographed using a gradient of AcOEt/Hexane 1:2 to 1:1 as eluent to give 470 mg (73% yield) of lactol. $^1$H-NMR (200 MHz, $CDCl_3$): 1.23 (t, J=7.1 Hz, 3H), 1.43 (t, J=3.3 Hz, 1H), 2.21–2.23 (m, 2H), 2.76 (d, J=3.0 Hz, 1H), 3.85 (d, J=8.7 Hz, 1H), 4.06 (d, J=8.7 Hz, 1H), 4.10 (c, J=7.1 Hz, 2H) and 5.32 (d, J=3.0 Hz, 1H). $^{13}$C-NMR (50 MHz, $CDCl_3$): 14.1, 22.1, 25.0, 31.2, 60.8, 67.3, 97.8 and 171.9 ppm.

Preparation 3

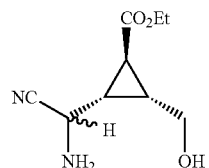

(2SR) and (2RS)-2-(1'SR, 2'RS, 3'RS)-2'-(ethoxycarbonyl)-3'-hydroxymethylcyclopropyl]glycinonitrile A suspension of ammonium chloride (2.42 g, 45.3 mmol) and neutral aluminium oxide (1.4 g) in acetonitrile (50 mL) was ultrasonicated for one hour. A solution of the product of Preparation 2 (780 mg, 4.53 mmol) in acetonitrile (20 mL) was then added and ultrasonicated for one hour. After potassium cyanide (3.54 g, 54.36 mmol) finely powdered was added, the mixture was allowed to react for 15 hours. Then, additional aluminium oxide (3.2 g) was added and the reaction mixture was ultrasonicated for 4 days. The mixture was then filtered through celite and the inorganics washed with acetonitrile to give 710 mg (78% yield) of the four possible aminonitriles as a yellow oil.

Preparation 4

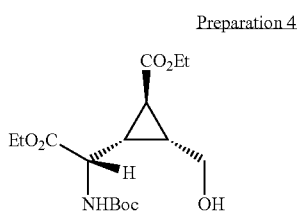

Ethyl (2SR, 1'SR, 2'RS, 3'RS)-N-(tert-butoxycarbonyl)-2-[2'-(ethoxycarbonyl)-3'-hydroxymethyl-cyclopropyl]glycinate A solution of the product of Preparation 3 (380 mg, 1.92 mmol) in ethanol saturated with hydrogen chloride (20 mL) and H$_2$O (0.10 mL, 5.75 mmol) was stirred for one hour at 0° C. and for 48 hours at room temperature. The following day, the solvent was removed in vacuo and the residue was dissolved in ethanol (25 mL). Then, the solution was neutralized with NaHCO$_3$ (solid), filtered through celite and concentrated to dryness. The resulting residue was taken into dioxane (20 mL), and a saturated aqueous solution of NaHCO$_3$ (5 mL) was added. Then, a solution of di-tert-butyldicarbonate (500 mg, 2.3 mmol) in dioxane (5 mL) was added and mixture stirred overnight. The layers were then separated and the aqueous layer was extracted with ethyl acetate (AcOEt). The combined organic layers were dried (Na$_2$SO$_4$), filtered and concentrated to dryness. The residue was purified by column chromatography using AcOEt/Hexane 1:2 as eluent to give 400 mg of a 1:2 mixture of diastereoisomers (61% overall yield). The minor and desired isomer (lower Rf) was separated by column chromatography using AcOEt/Hexane 1:3 as eluent giving rise to ethyl (2SR, 1'SR, 2'RS, 3'RS)-N-(tert-butoxycarbonyl)-2-[2'-(ethoxycarbonyl)-3'-hydroxymethyl-cyclopropyl]glycinate as a mixture of enantiomers.

Preparation 5

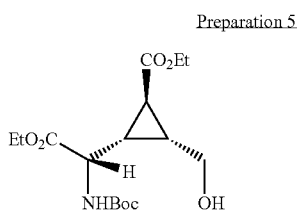

Ethyl (2SR, 1'SR, 2'RS, 3'RS)-N-(tert-butoxycarbonyl)-2-[2'-(ethoxycarbonyl)-3'-hydroxymethyl-cyclopropyl]glycinate A solution of the product of Preparation 2 (1.8 g, 10.45 mmol) in EtOH (65 mL) and NaOH (1N) (63 mL, 63.0 mmol) was stirred at 60° C. for 1 hour. The mixture was then cooled to 0° C. and the pH was adjusted to ~6 by addition of 1N KHSO$_4$. To the resulting solution, (NH$_4$)$_2$CO$_3$ (10.1 g, 104.5 mmol) and NaCN (1.02 g, 20.9 mmol) were added. The mixture was stirred under reflux overnight (16–17 hours) and then cooled to room temperature. The solution was then evaporated to dryness under vacuo to give a residue that was taken into MeOH and filtered off. The inorganics were washed with MeOH and the combined methanolic filtrates were concentrated in vacuo. The resulting residue was dissolved in 1N NaOH (200 mL) and the mixture was stirred under reflux for 48 hours and then cooled to 0° C. The pH was then adjusted to 1–2 by addition of 1N HCl, and the solvent was removed under vacuo.

The resulting residue was dissolved in a 1N HCl/ethanol solution (250 mL) and the mixture was stirred overnight at room temperature. The solvent was then removed under vacuo and the residue was taken into EtOH (200 mL). After the solvent was removed under vacuo, the residue was again taken into EtOH (200 mL) and the solution neutralized with NaHCO$_3$ (solid), the inorganics filtered off and the filtrate concentrated to dryness. The residue was taken into dioxane (200 mL) at room temperature and a saturated aqueous solution of NaHCO$_3$ (50 mL) was added. Then, a solution of di-tert-butyldicarbonate (2.75 g, 12.54 mmol) in dioxane (50 mL) was added dropwise and the mixture was vigorously stirred at room temperature overnight. The mixture was then diluted with AcOEt and the layers were separated. The aqueous layer was extracted with AcOEt (2X) and the combined organic layers were dried (Na$_2$SO$_4$), filtered and concentrated to dryness. The residue was purified by column chromatography using AcOEt/hexane (1:2) as eluent to give 2.15 g of a 2.3:1 mixture of diastereoisomers (60% overall yield). The major and desired isomer (lower Rf) was separated by column chromatography using Et$_2$O/Hexane 1:1 as eluent giving rise to ethyl (2SR, 1'SR, 2'RS, 3'RS)-N-(tert-butoxycarbonyl)-2-[2'-(ethoxycarbonyl)-3'-hydroxymethyl-clopropyl]glycinate as a mixture of enantiomers.

$^1$H-NMR (200 MHz, CDCl$_3$): 1.25 (t, J=7.1 Hz, 3H), 1.32 (t, J=7.1 Hz, 3H), 1.45 (s, 9H), 1.70–1.81 (m, 2H), 1.91–2.11 (m, 1H), 3.17 (dd, J=3.1, 10.1 Hz, 1H), 3.54–3.67 (m, 1H), 3.95–4.33 (m, 6H), and 5.20 (br d, J=7.3 Hz, 1H).

$^{13}$C-NMR (50 MHz, CDCl$_3$): 14.0, 14.1, 22.5, 28.2 (3C), 28.9, 29.2, 52.3, 60.8, 61.0, 62.5, 80.4, 155.3, 171.8 and 172.4 ppm.

Preparation 6

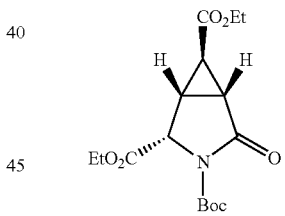

Ethyl (1SR, 2 SR, 5RS, 6RS)-3-tert-butoxycarbonyl-4-oxo-3-azabicyclo[3.1.0]-hexane-2,6-dicarboxylate To a solution of ethyl (2SR, 1'SR, 2'RS, 3'RS)-N-(tert-butoxycarbonyl)-2-[2'-(ethoxycarbonyl)-3'-(hydroxymethyl)-cyclopropyl]glycinate (740 mg, 2.14 mmol) in acetone (17 mL), Jones reagent solution was added dropwise at 0° C. The reaction mixture was stirred for 1 h at 0° C. and 2 h more at room temperature. Then water (17 mL) and isopropanol (17 mL) were added and the reaction mixture was extracted with ethyl acetate (3×20 mL). The combined organic layers were dried over MgSO$_4$ and the solvent removed under reduced pressure. The residue was purified by flash chromatography (ethyl acetate) to give 710 mg of the desired compound (97% yield).

$^1$H-NMR (200 MHz, CDCl$_3$) δ: 4.73 (d, 1H, J=5.9 Hz); 4.26 (dq, 2H, J=7.2 and 3.4 Hz); 2.62 (dt, 1H, J=3.2 and 6.6

Hz); 2.52 (dd, 1H, J=2.8 and 6.6 Hz); 2.32 (t, 1H, J=3.0 Hz); 1.44 (s, 9H); 1.27 (t, 3H, J=7.1 Hz) and (t, 3H, J=7.1 Hz) ppm.

$^{13}$C-NMR (50 MHz, CDCl$_3$) δ: 168.9, 168.7, 168.1, 148.1, 83.3, 61.7, 61.4, 58.1, 28.6, 27.2 (3C), 21.7, 21.5, 13.6 and 13.5 (2C) ppm.

IR (film): 3380, 2982, 1797, 1732, 1371, 1305, 1194, 1094, 1018 and 850 cm$^{-1}$.

EXAMPLE 1

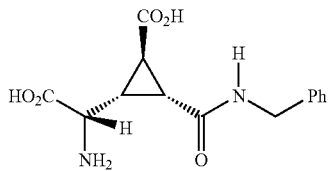

(2SR, 1'SR, 2'RS, 3'RS)-2-[2'-carboxy-3'-(phenylmethylaminocarbonyl)cyclopropyl]glycine a) Ethyl (2SR, 1'SR, 2'RS, 3'RS) N-(tert-butoxycarbonyl)-2-[2'-ethoxycarbonyl-3'-(phenylmethylaminocarbonyl)cyclopropyl]glycinate.

To a solution of ethyl (1SR, 2 SR, 5RS, 6RS) 3-tert-butoxycarbonyl-4-oxo-3-azabicyclo[3.1.0]hexane-2,6-dicarboxylate (307 mg, 0.9 mmol) in dry THF (7 mL) under argon was added benzylamine (590 μL, 5.4 mmol) and potassium cyanide (3 mg, 0.05 mmol). After stirring overnight in an ultrasonic bath, the solvent was removed under reduced pressure. The residue was directly purified by flash chromatography (hexane/ethyl acetate 3/1) to give 310 mg of the desired compound (80% yield).

1H-NMR (200 MHz, CDCl$_3$) δ: 7.23 (m, 5H); 7.01 (bt, 1H, J=5.5 Hz); 5.5 (bs, 1H); 4.36 (bt, 1H, J=9.9 Hz); 4.35 (m, 2H); 4.15–3.85 (m, 4H); 2.53 (bs, 1H); 2.25 (dd, 1H, J=9.3 and 4.8 Hz); 2.10 (bs, 1H); 1.39 (s, 9H) and 1.16 (dq, 6H, J=7.4 Hz) ppm.

13C-NMR (50 MHz, CDCl$_3$) δ: 172.1, 170.9, 168.0, 138.0, 128.4 (2C), 127.7 (2C), 127.2, 80.0, 61.0, 60.2, 51.2, 43.7, 29.5, 28.8 (3C), 28.0, 26.0 and 14.0 (2C) ppm.

IR (KBr): 3366, 2980, 1726, 1653, 1522, 1456, 1394, 1370, 1337, 1248, 1174, 1028 and 700 cm-1.

b) (2SR, 1'SR, 2'RS, 3'RS)-2-[2'-carboxy-3'-(phenylmethylaminocarbonyl)cyclopropyl]glycine.

To a solution of ethyl (2SR, 1'SR, 2'RS, 3'RS) N-(tert-butoxycarbonyl)-2-[2'-ethoxycarbonyl-3'-(phenylmethylaminocarbonyl)cyclopropyl]glycinate (300 mg, 0.71 mmol) in THF (7 mL) was added a solution of 2.5N LiOH (15 mL). The mixture was stirred for 5 h at rt. Then solvent was removed under reduced pressure and the aqueous phase was acidified with 1N HCl until pH=1 and the mixture was extracted with Et$_2$O. The combined organic phases were dried (MgSO$_4$) and evaporated under reduced pressure. Then, a solution of HCl/AcOEt 1N (6 mL) was added, and the mixture was stirred overnight. Solvent was evaporated in vacuo affording the corresponding hydrochloride. The final aminoacid (82 mg, 50% yield) was isolated as zwitterion by ion exchange chromatography.

1H-NMR (200 MHz, D$_2$O) δ: 1.90 (m, 1H); 2.07 (t, 1H, J=5.4 Hz); 2.17 (dd, 1H, J=4.1 and 10.7 Hz); 3.82 (d, 1H, J=10.5 Hz); 4.10 (AB system, 2H, J=12.2 Hz) and 7.02 (m, 5H) ppm.

13C-NMR (50 MHz, Py-d5) δ: 177.9; 173.2; 170.8; 128.7 (2C); 127.5 (2C); 127.2; 52.4; 43.4; 27.8 (2C) and 27.7 ppm.

IR (KBr): 3408, 3287, 3071, 2961, 1713, 1635, 1557, 1395, 1331 and 1234 cm-1.

EXAMPLE 2

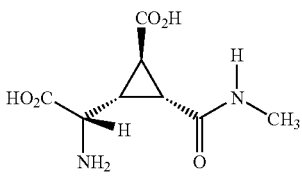

(2SR, 1'SR, 2'RS, 3'RS)-2-[2'-carboxy-3'-(methylaminocarbonyl)cyclopropyl]glycine a) Ethyl (2SR, 1'SR, 2'RS, 3'RS) N-(tert-butoxycarbonyl)-2-[2'-ethoxycarbonyl-3-(methylaminocarbonyl)cyclopropyl]glycinate.

To a solution of ethyl (1SR, 2 SR, 5RS, 6RS) 3-tert-butoxycarbonyl-4-oxo-3-azabicyclo[3.1.0]hexane-2,6-dicarboxylate (312 mg, 0.9 mmol) in dry THF (6 mL) under argon was added methylamine (2.74 mL, 5.4 mmol) and potassium cyanide (3 mg, 0.05 mmol). After stirring overnight in an ultrasonic bath, the solvent was removed under reduced pressure. The residue was directly purified by flash chromatography (hexane/ethyl acetate 1/1) to give 272 mg of the desired compound (80% yield).

$^1$H-NMR (200 MHz, CDCl$_3$) δ: 6.00 (d, 1H); 5.22 (s, 1H); 4.53 (t, 1H, J=8.6 Hz); 4.13 (c, 4H); 2.82 (d, 3H); 2.59 (s, 1H); 2.25 (d, 1H, J=4.7 Hz); 1.91 (s, 1H); 1.43 (s 9H) and 1.24 (t, 6H) ppm.

$^{13}$C-NMR (50 MHz, CDCl$_3$) δ: 172.3; 171.5; 169.0; 155.0; 80.4; 61.9; 61.6; 51.8; 30.6; 29.5; 28.6 (3C); 27.1; 25.7 and 14.5 (2C) ppm.

b) (2SR, 1'SR, 2'RS, 3'RS)-2-[2'-carboxy-3'-(methylaminocarbonyl)-cyclopropyl]glycine.

To a solution of ethyl (2SR, 1'SR, 2'RS, 3'RS) N-(tert-butoxycarbonyl)-2-[2'-ethoxycarbonyl-3'-(methylaminocarbonyl)cyclopropyl]glycinate (190 mg, 0.51 mmol) in THF (5 mL) was added a solution of 2.5N LiOH (8 mL). The mixture was stirred for 20 h at rt. The organic layer was separated and discarded and the aqueous layer was washed with Et$_2$O. The aqueous phase was adjusted to pH=1 by addition of 1N HCl at 0° C., it was extracted four times with AcOEt, and the combined organic layers were dried (MgSO$_4$) and evaporated under reduced pressure. Then, a solution of HCl/AcOEt 1N (4 mL) was added, and the mixture was stirred overnight. Solvent was evaporated in vacuo affording the corresponding hydrochloride. The final aminoacid (55 mg, 50% yield) was isolated as zwitterion by ion exchange chromatography.

1H-NMR (200 MHz, D$_2$O/Py-d5) δ: 3.65 (d, 1H, J=10.5 Hz); 2.28 (s, 3H) and 1.97–1.62 (m, 1H) and 1.75–1.62 (m, 1H) ppm 13C-NMR (50 MHz, D$_2$O/Py-d5) δ: 177.5; 172.7; 170.7; 51.7; 27.5; 27.4; 26.9 and 25.7 ppm.

IR (film): 3379, 3101, 1643, 1572, 1385, 1327, 1242, 1172, 1103, 1055, 1030 and 951 cm-1.

EXAMPLE 3

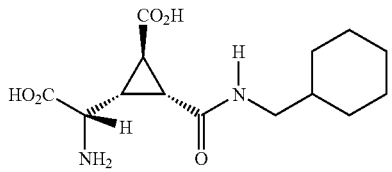

(2SR,1'SR,2'RS,3'RS)-2-[2'-carboxy-3'-(cyclohexyl-methylaminocarbonyl)cyclopropyl]glycine a) Ethyl (2SR, 1'SR, 2'RS, 3'RS)N-(tert-butoxycarbonyl)-2-[3'-(cyclohexylmethylaminocarbonyl)-2'-(ethoxycarbonyl) cyclopropyl]glycinate.

A suspension of a mixture of ethyl (2SR, 1'SR, 2'RS, 3'RS)N-(tert-butoxycarbonyl)-2-[2'-ethoxycarbonyl-3'-(phenylmethylaminocarbonyl)cyclopropyl]glycinate (232 mg, 0.54 mmol) and $PtO_2$ (12 mg) in EtOH (5 mL) was stirred under hydrogen atmosphere for 7 days. The catalyst was then filtered off through celite and the solvent was removed under vacuo affording the desired compound (230 mg, 98% yield).

$^1$H-NMR (200 MHz, $CDCl_3$) δ: 6.15 (bs, 1H); 5.24 (bs, 1H); 4.50 (dd, 1H); 4.20–4.04 (m, 4H); 3.17–2.97 (m, 2H); 2.53 (t, 1H); 2.20–2.04 (m, 2H); 1.69 (m, 5H); 1.42 (s, 9H); 1.30-1.12 (m, 8H) and 0.91 (m, 4H) ppm.

$^{13}$C-NMR (50 MHz, $CDCl_3$).: 172.1; 171.0; 167.9; 155.0; 79.8; 61.4; 61.1; 50.5; 46.2; 37.8; 30.7; 30.2; 29.6(2C); 29.1; 28.1(3C); 26.3; 25.7; 25.1 and 14.0 (2C) ppm.

b) (2SR,1'SR,2'RS,3'RS)-2-[2'-carboxy-3'-(cyclohexylm-ethylaminocarbonyl)cyclopropyl]-glycine.

To a solution of ethyl (2SR,1'SR,2'RS,3'RS)-N-(tert-butoxycarbonyl)-2-[3'-(cyclohexylmethylaminocarbonyl)-2'-(ethoxycarbonyl)cyclopropyl]glycinate (101 mg, 0.23 mmol) in THF (2 mL) was added a solution of 2.5N LiOH (4 mL). The mixture was stirred for 20 h at rt. The organic layer was separated and discarded and the aqueous layer was washed with $Et_2O$. The aqueous phase was adjusted to pH=1 by addition of 1N HCl at 0° C., it was extracted four times with AcOEt, and the combined organic layers were dried ($MgSO_4$) and evaporated under reduced pressure. Then, a solution of HCl/AcOEt 1N (2.3 mL) was added, and the mixture was stirred overnight. Solvent was evaporated in vacuo affording the corresponding hydrochloride. The final aminoacid (35 mg, 50% yield) was isolated as zwitterion by ion exchange chromatography.

$^1$H-NMR (200 MHz, $D_2O$/Py-d5) δ: 4.30 (d, 1H, J=10.2 Hz); 3.19–2.90 (m, 2H); 2.74–2.67 (m, 1H); 2.58 (t, 1H, J=5.1 Hz); 2.43–2.30 (m, 1H); 1.65–1.39 (m, 6H) and 1.13–0.71 (m, 5H) ppm.

$^{13}$C-NMR (50 MHz, $D_2O$/Py-d5) δ: 177.3; 172.5; 169.9; 51.8; 45.4; 36.5; 29.6(2C); 27.7; 27.3; 27.0; 25.3 and 24.7(2C) ppm.

IR (film): 3308, 2926, 2853, 1713, 1639, 1566, 1448, 1390, 1331, 1257, 1234, 1190, 1151, 1099, 1030 and 987 $cm^{-1}$.

EXAMPLE 4

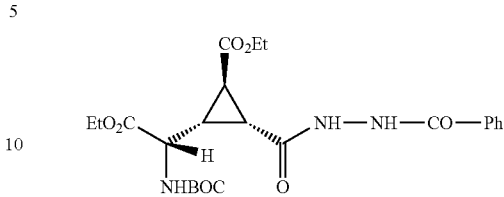

(2SR, 1'SR, 2'RS, 3'RS)-2-[3'-(benzoylhydrazi-nocarbonyl)-2'-carboxycyclopropyl]glycine a) Ethyl (2SR, 1'SR, 2'RS, 3'RS)N-(tert-butoxycarbonyl)-2-[3'-(benzoylhydrazinocarbonyl)-2'-(ethoxycarbonyl) cyclopropyl]glycinate.

To a solution of ethyl (1SR, 2 SR, 5RS, 6RS) 3-tert-butoxycarbonyl-4-oxo-3-azabicyclo[3.1.0]hexane-2,6-dicarboxylate (88 mg, 0.25 mmol) in dry THF (2 mL) under argon was added benzoic hydrazide (209 mg, 1.54 mmol) and potassium cyanide (0.83 mg, 0.01 mmol). After stirring overnight in an ultrasonic bath, the solvent was removed under reduced pressure. The residue was directly purified by flash chromatography (hexane/ethyl acetate 1/1) to give 84 mg of the desired compound (72% yield).

$^1$H-NMR (200 MHz, $CDCl_3$) δ: 7.81 (d, 2H, J=7.0 Hz); 7.48–7.25 (m, 3H); 5.42 (bs, 1H, J=7.5 Hz); 4.49 (t, 1H, J=4.4 Hz); 4.14–4.02 (m, 4H); 2.68–2.62 (m, 2H); 2.14 (m, 1H); 1.41 (s, 9H) and 1.21 (dt, 6H) ppm.

$^{13}$C-NMR (50 MHz, $CDCl_3$) δ: 171.3; 170.9; 165.7; 164.0; 155.1; 132.2; 131.1; 128.6; 128.5; 127.4; 79.9; 61.7; 61.2; 50.4; 30.8; 28.1 (3C); 26.7; 25.5; 14.0 and 13.8 ppm.

b) (2SR, 1'SR, 2'RS, 3'RS)-2-[3'-(benzoylhydrazinocarbo-nyl)-2'-carboxycyclopropyl]glycine.

To a solution of ethyl (2SR, 1'SR, 2'RS, 3'RS)N-(tert-butoxycarbonyl)-2-[3'-(benzoylhydrazinocarbonyl)-2'-(ethoxycarbonyl)cyclopropyl]glycinate (143 mg, 0.31 mmol) in THF (3 mL) was added a solution of 2.5N LiOH (6 mL). The mixture was stirred for 20 h at rt. The organic layer was separated and discarded and the aqueous layer was washed with Et2O. The aqueous phase was adjusted to pH=1 by addition of 1N HCl at 0° C., it was extracted four times with AcOEt, and the combined organic layers were dried ($MgSO_4$) and evaporated under reduced pressure. Then, a solution of HCl/AcOEt 1N (2.5 mL) was added, and the mixture was stirred overnight. Solvent was evaporated in vacuo affording the corresponding hydrochloride. The final aminoacid (45 mg, 44% yield) was isolated as zwitterion by ion exchange chromatography.

$^1$H-NMR (200 MHz, $D_2O$/Py-d5) δ: 7.45 (d, 2H); 7.18–7.05 (m, 3H); 3.89 (d, 1H, J=8.8 Hz) and 2.04–1.63 (m, 3H) ppm $^{13}$C-NMR (50 MHz, $D_2O$/Py-d5) δ: 177.1; 175.5; 171.8; 168.7; 130.9; 130.5; 130.2; 126.9; 125.5; 125.0; 50.6; 28.1; 26.6 and 25.3 ppm. IR (film): 3433, 3202, 1713, 1709, 1693, 1631, 1392, 1230, 1028 and 974 $cm^{-1}$.

EXAMPLE 5

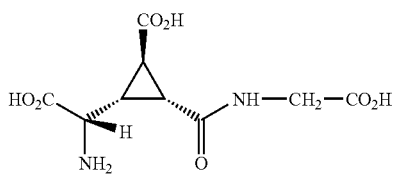

(2SR, 1'SR, 2'RS, 3'RS)-2-[2'-carboxy-3'-(carboxymethylaminocarbonyl)cyclopropyl]glycine a) Ethyl (2SR, 1'SR, 2'RS, 3'RS)N-(tert-butoxycarbonyl)-2-[3'-(ethoxycarbonylmethylaminocarbonyl)-2'-(ethoxycarbonyl)cyclopropyl]glycinate.

To a solution of ethyl (1SR, 2SR, 5RS, 6RS) 3-tert-butoxycarbonyl-4-oxo-3-azabicyclo[3.1.0]hexane-2,6-dicarboxylate (190 mg, 0.55 mmol) in dry THF (3.5 mL) under argon was added ethyl glycinate hydrochloride (466 mg, 3.34 mmol), potassium cyanide (1.7 mg, 0.02 mmol) and $Et_3N$ (0.44 mL, 3.34 mmol). After stirring overnight in an ultrasonic bath, the solvent was removed under reduced pressure. The residue was directly purified by flash chromatography (hexane/ethyl acetate 1/1) to give 235 mg of the desired compound (95% yield).

$^1$H-NMR (200 MHz, CDCl$_3$) δ: 6.71 (bs, 1H); 5.26 (bs, 1H); 4.48 (t, 1H); 4.22–3.96 (m, 8H); 2.55 (t, 1H, J=5.1 Hz); 2.32–2.25 (m, 1H); 2.12 (m, 1H); 1.4 (s, 9H) and 1.27–1.14 (dt, 9H) ppm.

$^{13}$C-NMR (50 MHz, CDCl$_3$) δ: 171.7; 170.9; 169.7; 168.2; 154.9; 79.9; 61.1; 60.7; 60.3; 50.5; 41.4; 30.5; 28.6 (3C); 28.1; 25.4; 14.0 and 13.9 ppm b) (2SR, 1'SR, 2'RS, 3'RS)-2-[2'-carboxy-3'-(carboxymethylaminocarbonyl)cyclopropyl]glycine.

To a solution of ethyl (2SR, 1'SR, 2'RS, 3'RS)N-(tert-butoxycarbonyl)-2-[3'-(ethoxycarbonylmethylaminocarbonyl)-2'-(ethoxycarbonyl)cyclopropyl]glycinate (248 mg, 0.55 mmol) in THF (5 mL) was added a solution of 2.5N LiOH (8 mL). The mixture was stirred for 20 h at rt. The organic layer was separated and discarded and the aqueous layer was washed with Et$_2$O. The aqueous phase was adjusted to pH=1 by addition of 1N HCl at 0° C., it was extracted four times with AcOEt, and the combined organic layers were dried (MgSO$_4$) and evaporated under reduced pressure. Then, a solution of HCl/AcOEt 1N (4 mL) was added, and the mixture was stirred overnight. Solvent was evaporated in vacuo affording the corresponding hydrochloride. The final aminoacid (57 mg, 40% yield) was isolated as zwitterion by ion exchange chromatography.

$^1$H-NMR (200 MHz, D$_2$O/Py-d5) δ: 4.19 (d, 1H, J=10 Hz); 3.83 (bs, 2H) and 2.56–2.15 (m, 3H) ppm.

$^{13}$C-NMR (50 MHz, D$_2$O/Py-d5) δ: 177.1; 175.4; 172.4; 169.9; 51.4; 43.1; 27.3; 26.8 and 26.5 ppm.

IR (film): 3078, 1577, 1392, 1234, 1103, 1030 and 956 cm$^{-1}$.

EXAMPLE 6

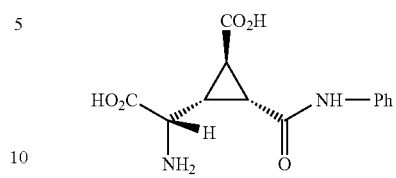

(2SR, 1'SR, 2'RS, 3'RS)-2-[2'-carboxy-3'-(phenylaminocarbonyl)cyclopropyl]glycine a) Ethyl (2SR, 1'SR, 2'RS, 3'RS)N-(tert-butoxycarbonyl)-2-[2'-ethoxycarbonyl-3'-(phenylaminocarbonyl)cyclopropyl]glycinate.

To a solution of AlCl$_3$ (53.8 mg, 0.40 mmol) in dry CH2Cl2 (1 mL) at 0° C., aniline (70 μl, 0.77 mmol) in CH$_2$Cl$_2$ (0.5 mL) was added dropwise. The mixture was stirred at room temperature for 10 min, and then ethyl (1SR, 2 SR, 5RS, 6RS) 3-tert-butoxycarbonyl-4-oxo-3-azabicyclo [3.1.0]hexane-2,6-dicarboxylate (106 mg 0.31 mmol) in dry CH$_2$Cl$_2$ (0.5 mL) was added. After stirring at room temperature for 4 h, a mixture of ice and water was added. The layers were separated and the aqueous phase was extracted with CH$_2$Cl$_2$ (X3). The combined organic layers were dried over MgSO$_4$ and the solvent removed under reduced pressure. The residue was purified by flash chromatography (hexane/ethyl acetate 1/1) to give 67.5 mg of the desired compound (50% yield).

$^1$H-NMR (200 MHz, CDCl$_3$) δ: 7.50 (d, 2H); 7.25–7.15 (m, 3H); 5.43 (bd, 1H); 4.61 (t, 1H); 4.10 (m, 4H); 2.70 (t, 1H); 2.40 (m, 1H); 2.10 (bs, 1H); 1.45 (s, 9H); 1.20 (t, 3H) and 1.10 (t, 3H) ppm.

$^{13}$C-NMR (50 MHz, CDCl$_3$) δ: 172.3; 171.2; 166.2; 155.0; 138.0; 129.2; 128.8; 124.1; 119.7; 115.0; 79.9; 61.7; 61.4; 50.5; 30.8; 29.8; 28.1 (3C); 25.5; 14.0 and 13.8 ppm.

b) (2SR, 1'SR, 2'RS, 3'RS)-2-[2'-carboxy-3'-(phenylaminocarbonyl)cyclopropyl]glycine.

To a solution of ethyl (2SR, 1'SR, 2'RS, 3'RS) N-(tert-butoxycarbonyl)-2-[2'-ethoxycarbonyl-3'-(phenylaminocarbonyl)cyclopropyl]glycinate (70 mg, 0.16 mmol) in THF (1.6 mL) was added a solution of 2.5N LiOH (3.2 mL). The mixture was stirred for 20 h at rt. The organic layer was separated and discarded and the aqueous layer was washed with Et$_2$O. The aqueous phase was adjusted to pH=1 by addition of 1N HCl at 0° C., it was extracted four times with AcOEt, and the combined organic layers were dried (MgSO$_4$) and evaporated under reduced pressure. Then, a solution of HCl/AcOEt 1N (1.3 mL) was added, and the mixture was stirred overnight. Solvent was evaporated in vacuo affording the corresponding hydrochloride. The final aminoacid (20 mg, 45% yield) was isolated as zwitterion by ion exchange chromatography.

$^1$H-NMR (200 MHz, D$_2$O/Py-d5) δ: 7.99 (d, 2H); 7.52 (m, 3H); 4.65 (d, 1H, J=10 Hz); 3.17 (m, 1H); 2.98 (m, 1H) and 2.81 (m, 1H) ppm.

$^{13}$C-NMR (50 MHz, D$_2$O/Py-d5) δ: 177.9; 173.1; 169.2; 137.3; 129.0; 124.8; 124.2; 120.9; 120.7; 52.3; 28.6; 28.3 and 28.1 ppm.

IR (film): 3059, 2926, 2855, 1711, 1658, 1631, 1601, 1550, 1500, 1444, 1383, 1313, 1234, 1169, 1028 and 989 cm$^{-1}$.

EXAMPLE 7

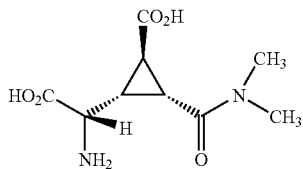

(2SR, 1'SR, 2'RS, 3'RS)-2-[2'-carboxy-3'-(dimethylaminocarbonyl)cyclopropyl]glycine a) Ethyl (2SR, 1'SR, 2'RS, 3'RS)N-(tert-butoxycarbonyl)-2-[2'-ethoxycarbonyl-3'-(dimethylaminocarbonyl)-cyclopropyl]-glycinate.

To a solution of $AlCl_3$ (119.8 mg, 0.89 mmol) in dry $CH_2Cl_2$ (2 mL) at 0° C., dimethylamine (solution 2M/THF) (0.82 mL 1.64 mmol) was added dropwise. The mixture was stirred at room temperature for 10 min, and then ethyl (1SR, 2SR, 5RS, 6RS) 3-tert-butoxycarbonyl-4-oxo-3-azabicyclo[3.1.0]hexane-2,6-dicarboxylate (234 mg, 0.68 mmol) in dry $CH_2Cl_2$ (2 mL) was added. After stirring at room temperature for 30 min, a mixture of ice and water was added. The layers were separated and the aqueous phase was extracted with $CH_2Cl_2$ (X3). The combined organic layers were dried over $MgSO_4$ and the solvent removed under reduced pressure. The residue was purified by flash chromatography (hexane/ethyl acetate 1/1.5) to give 236 mg of the desired compound (89% yield).

$^1$H-NMR (200 MHz, $CDCl_3$) δ: 5.91 (bs, 1H); 4.63–4.27 (m, 4H); 2.84 (s, 3H); 2.57 (s, 3H); 2.14 (t, 1H); 1.94(m, 1H); 1.31 (m, 1H); 1.32 (s, 9H) and 1.10 (t, 6H) ppm.

$^{13}$C-NMR (50 MHz, $CDCl_3$) δ: 172.0; 170.9; 167.6; 155.0; 79.7; 61.5; 61.3; 51.0; 37.4; 35.9; 31.4; 28.1 (3C); 22.5; 20.9 and 14.0 (2C) ppm.

b) (2SR, 1'SR, 2'RS, 3'RS)-2-[2'-carboxy-3'-(dimethylaminocarbonyl)cyclopropyl]glycine.

To a solution of ethyl (2SR, 1'SR, 2'RS, 3'RS)N-(tert-butoxycarbonyl)-2-[2'-ethoxycarbonyl-3'-(dimethylaminocarbonyl)cyclopropyl]glycinate (73 mg, 0.18 mmol) in THF (2 mL) was added a solution of 2.5N LiOH (3 mL). The mixture was stirred for 35 min at rt. The organic layer was separated and discarded and the aqueous layer was washed with $Et_2O$. The aqueous phase was adjusted to pH=1 by addition of 1N HCl at 0° C., it was extracted four times with AcOEt, and the combined organic layers were dried ($MgSO_4$) and evaporated under reduced pressure. Then, a solution of HCl/AcOEt 1N (1.3 mL) was added, and the mixture was stirred for 1 h. Solvent was evaporated in vacuo affording the corresponding hydrochloride. The final aminoacid (29 mg, 69% yield) was isolated as zwitterion by ion exchange chromatography.

$^1$H-NMR (200 MHz, $D_2O$/Py-d5) δ: 3.59 (d, 1H, J=10.7 Hz); 3.03 (s, 3H); 2.82 (s, 3H); 2.52–2.45(m, 1H); 2.33(t, 1H, J=5.3 Hz) and 2.17–2.07 (m, 1H) ppm.

$^{13}$C-NMR (50 MHz, $D_2O$/Py-d5) δ: 177.7; 172.5; 169.4; 52.6; 37.1; 35.4; 29.8; 27.2 and 25.5 ppm.

IR (film): 3437, 3036, 1631, 1560, 1539, 1489, 1423, 1392, 1332, 1147 and 908 cm$^{-1}$.

EXAMPLE 8

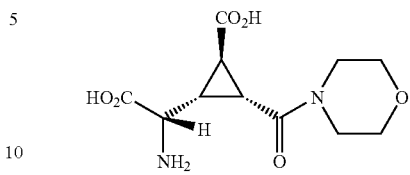

(2SR, 1'SR, 2'RS, 3'RS)-2-[2'-carboxy-3'-(morpholinylcarbonyl)cyclopropyl]glycine a) Ethyl (2SR, 1'SR, 2'RS, 3'RS)N-(tert-butoxycarbonyl)-2-[2'-ethoxycarbonyl-3'-(morpholinylcarbonyl)cyclopropyl]-glycinate.

To a solution of $AlCl_3$ (73 mg, 0.54 mmol) in dry $CH_2Cl_2$ (3 mL) at 0° C., morpholine (90 μl, 1.04 mmol) in dry $CH_2Cl_2$ (3 mL) was added dropwise. The mixture was stirred at room temperature for 20 min, and then ethyl (1SR, 2SR, 5RS, 6RS) 3-tert-butoxycarbonyl-4-oxo-3-azabicyclo[3.1.0]hexane-2,6-dicarboxylate (143 mg, 0.41 mmol) in dry $CH_2Cl_2$ (1 mL) was added. After stirring at room temperature for 1 h, a mixture of ice and water was added. The layers were separated and the aqueous phase was extracted with $CH_2Cl_2$. The combined organic layers were dried over $MgSO_4$ and the solvent removed under reduced pressure. The residue was purified by flash chromatography (hexane/ethyl acetate 1/1) to give 126 mg of the desired compound (70% yield).

$^1$H-NMR (200 MHz, $CDCl_3$) δ: 5.30 (bs, 1H); 4.10 (m, 4H); 3.60 (m, 8H); 2.60 (t, 1H); 2.45 (m, 1H); 2.10 (m, 1H); 1.40 (s, 9H) and 1.2 (m, 6H) ppm.

$^3$C-NMR (50 MHz, $CDCl_3$) δ: 172.0; 170.7; 166.2; 155.0; 79.8; 66.6; 66.4; 61.4; 61.1; 51.1; 46.0; 42.5; 31.4; 28.1 (3C); 22.5; 20.9; 14.2 and 14.1 ppm.

b) (2SR, 1'SR, 2'RS, 3'RS)-2-[2'-carboxy-3'-(morpholinylcarbonyl)cyclopropyl]glycine.

To a solution of ethyl (2SR, 1'SR, 2'RS, 3'RS)N-(tert-butoxycarbonyl)-2-[2'-ethoxycarbonyl-3'-(morpholinylcarbonyl)cyclopropyl]glycinate (126 mg, 0.29 mmol) in THF (2.9 mL) was added a solution of 2.5N LiOH (4 mL). The mixture was stirred for 20 h at rt. The organic layer was separated and discarded and the aqueous layer was washed with Et2O. The aqueous phase was adjusted to pH=1 by addition of 1N HCl at 0° C., it was extracted four times with AcOEt, and the combined organic layers were dried ($MgSO_4$) and evaporated under reduced pressure. Then, a solution of HCl/AcOEt 1N (2.3 mL) was added, and the mixture was stirred overnight. Solvent was evaporated in vacuo affording the corresponding hydrochloride. The final aminoacid (60 mg, 75% yield) was isolated as zwitterion by ion exchange chromatography.

$^1$H-NMR (200 MHz, $D_2O$/Py-d5) δ: 3.57 (m, 1H); 3.28 (m, 8H); 2.26 (m, 1H); 2.12 (t, 1H; J=8.6 Hz) and 1.86 (m, 1H) ppm. $^{13}$C-NMR (50 MHz, $D_2O$/Py-d5) δ: 178.1; 172.9; 168.7; 66.2; 66.1; 53.1; 46.1; 42.6; 28.4; 28.1 and 25.6 ppm.

IR (film): 3429, 3071, 1633, 1620, 1388, 1238, 1111, 1041 and 895 cm$^1$.

EXAMPLE 9

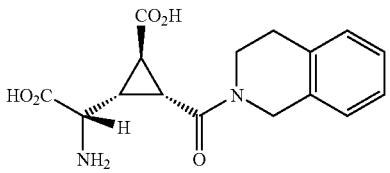

(2SR, 1'SR, 2'RS, 3'RS)-2-[2'-carboxy-3'-(tetrahydroisoquinolylcarbonyl)cyclopropyl]glycine a) Ethyl (2SR, 1'SR, 2'RS, 3'RS)N-(tert -butoxycarbonyl)-2-[2'-ethoxycarbonyl-3'-(tetrahydroisoquinolylcarbonyl)cyclopropyl]glycinate.

To a solution of $AlCl_3$ (48.7 mg, 0.36 mmol) in dry $CH_2Cl_2$ (1 mL) at 0° C., tetrahydroisoquinoline (88 μl, 0.70 mmol) in $CH_2Cl_2$ (1 mL) was added dropwise. The mixture was stirred at room temperature for 10 min, and then ethyl (1SR, 2SR, 5RS, 6RS) 3-tert-butoxycarbonyl-4-oxo-3-azabicyclo[3.1.0]hexane-2,6-dicarboxylate (96 mg, 0.28 mmol) in dry $CH_2Cl_2$ (1 mL) was added. After stirring at room temperature for 3 h, a mixture of ice and water was added. The layers were separated and the aqueous phase was extracted with $CH_2Cl_2$. The combined organic layers were dried over $MgSO_4$ and the solvent removed under reduced pressure. The residue was purified by flash chromatography (hexane/ethyl acetate 2/1) to give 95 mg of the desired compound (71% yield).

$^1$H-NMR (200 MHz, $CDCl_3$) δ: 7.12 (m, 4H); 4.77 (m, 1H); 4.24 3.50 (m, 8H); 2.89–2.58 (m, 4H); 2.30 (m, 1H); 1.4 (s, 9H) and 1.20 (t, 6H) ppm. $^{13}$C-NMR (50 MHz, $CDCl_3$) δ: 172.1; 170.8; 166.6; 134.3; 132.3; 128.7; 128.0; 126.6; 126.5; 61.4; 61.1; 50.7; 47.2; 44.8; 43.5; 30.8; 29.3; 28.5; 28.1 (3C); 14.0 and 13.9 ppm.

b) (2SR, 1'SR, 2'RS, 3'RS)-2-[2'-carboxy-3'-(tetrahydroisoquinolylcarbonyl)cyclopropyl]glycine.

To a solution of ethyl (2SR, 1'SR, 2'RS, 3'RS) N-(tert-butoxycarbonyl)-2-[2'-ethoxycarbonyl-3'-(tetrahydroisoquinolylcarbonyl)cyclopropyl]glycinate (75 mg, 0.15 mmol) in THF (1.6 mL) was added a solution of 2.5N LiOH (2.5 mL). The mixture was stirred for 2 h at rt. The organic layer was separated and discarded and the aqueous layer was washed with $Et_2O$. The aqueous phase was adjusted to pH=1 by addition of 1N HCl at $O_2C$, it was extracted four times with AcOEt, and the combined organic layers were dried ($MgSO_4$) and evaporated under reduced pressure. Then, a solution of HCl/AcOEt 1N (1.3 mL) was added, and the mixture was stirred overnight. Solvent was evaporated in vacuo affording the corresponding hydrochloride. The final aminoacid (31 mg, 61% yield) was isolated as zwitterion by ion exchange chromatography.

$^1$H-NMR (200 MHz, $D_2O$/Py-d5) δ: 6.70 (m, 4H); 4.20–3.23 (m, 5H) and 2.28–2.07 (m, 5H) ppm. $^{13}$C—NMR (50 MHz, $D_2O$/Py-d5) δ: 177.0; 171.9; 167.8; 133.9; 131.5; 127.5; 125.9; 52.1; 46.2; 43.8; 42.9; 27.3; 27.0 and 25.3 ppm. IR (film): 3426, 3028, 2928, 1711, 1620, 1581, 1452, 1385, 1242, 1113 and 929 $cm^{-1}$.

EXAMPLE 10

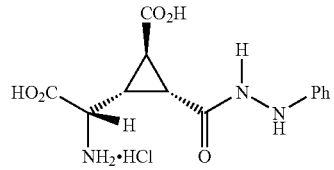

(2SR, 1'SR, 2'RS, 3'RS)-2-[2'-carboxy-3'-(phenylhydrazinocarbonyl)cyclopropyl]glycine hydrochloride a) Ethyl (2SR, 1'SR, 2'RS, 3'RS) N-(tert-butoxycarbonyl)-2-[2'-ethoxycarbonyl-3'-(phenylhydrazinocarbonyl)cyclopropyl]glycinate.

To a solution of ethyl (1SR, 2SR, 5RS, 6RS) 3-tert-butoxycarbonyl-4-oxo-3-azabicyclo[3.1.0]hexane-2,6-dicarboxylate (202 mg, 0.59 mmol) in dry THF (4 mL) under argon was added phenylhydrazine (0.35 mL, 3.55 mmol) and potassium cyanide (1.88 mg, 0.02 mmol). After stirring overnight in an ultrasonic bath, the solvent was removed under reduced pressure. The residue was directly purified by flash chromatography (hexane/ethyl acetate 2/1) to give 106 mg of the desired compound (40% yield).

$^1$H-NMR (200 MHz, $CDCl_3$) δ: 8.56 (d, J=3 Hz, 1H); 7.17–7.10 (t, 2H); 6.85–6.76 (m, 3H); 6.29 (bs, 1H); 5.34 (bs, 1H); 4.44–4.35 (dd, 1H); 4.15–4.04 (m, 4H); 2.55–2.50 (t, 1H); 2.41–2.34 (dd, 1H); 2.21 (bs, 1H); 1.40 (s, 9H); 1.21–1.16 (m, 6H) ppm. $^{13}$C-NMR (50 MHz, $CDCl_3$) δ: 171.8, 170.9, 168.8, 155.0, 147.9, 129.1, 128.9, 120.7, 113.5, 112.8, 79.9, 61.5, 61.2, 50.6, 30.7, 28.1, 26.8, 25.3, 13.9 ppm.

b) (2SR, 1'SR, 2'RS, 3'RS)-2-[2'-carboxy-3'-(phenylhydrazinocarbonyl)cyclopropyl]glycine Hydrochloride.

To a solution of ethyl (2SR, 1'SR, 2'RS, 3'RS)N-(tert -butoxycarbonyl)-2-[2'-ethoxycarbonyl-3'-(phenylhydrazinocarbonyl)cyclopropyl]glycinate (95 mg, 0.21 mmol) in THF (2 mL) was added a solution of 2.5N LiOH (3 mL). The mixture was stirred for 18 h at rt. Then solvent was removed under reduced pressure and the aqueous phase was acidified with 1N HCl until pH=1 and the mixture was extracted with $Et_2O$. The combined organic phases were dried ($MgSO_4$) and evaporated under reduced pressure. Then, a solution of HCl/AcOEt 1N (2 mL) was added, and the mixture was stirred overnight. Solvent was evaporated in vacuo affording 34 mg (50% yield) of the corresponding hydrochloride.

$^{13}$C-NMR. (50 MHz, Methanol-d4) δ: 173.2, 172.6, 170.7, 149.5, 130.0, 121.2, 114.2, 114.0, 51.2, 27.8, 27.6, 26.5 ppm.

EXAMPLE 11

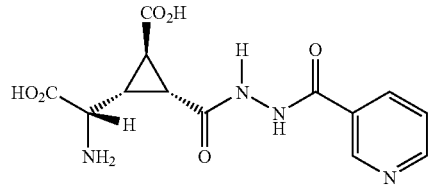

(2SR, 1'SR, 2'RS, 3'RS)-2-[2'-carboxy-3'-(3''-pyridylcarbonylhydrazinocarbonyl)cyclopropyl]glycine a) Ethyl (2SR, 1'SR, 2'RS, 3'RS)N-(tert-butoxycarbonyl)-2-[2'-ethoxycarbonyl-3'-(3''-pyridylcarbonylhydrazinocarbonyl) cyclopropyl]glycinate.

To a solution of ethyl (1SR, 2 SR, 5RS, 6RS) 3-tert-butoxycarbonyl-4-oxo-3-azabicyclo[3.1.0]hexane-2,6-dicarboxylate (156 mg, 0.45 mmol) in dry THF (3 mL) under argon was added nicotinic hydrazide (376 mg, 2.74 mmol) and potassium cyanide (1.48 mg, 0.02 mmol). After stirring overnight in an ultrasonic bath, the solvent was removed under reduced pressure. The residue was directly purified by flash chromatography (hexane/ethyl acetate 1/1) to give 105 mg of the desired compound (48% yield).

$^1$H-NMR (200 MHz, CDCl$_3$) δ: 9.03 (s, 1H); 8.68 (d, J=3.5 Hz, 1H); 8.15 (d, J=8.1 Hz, 1H); 7.33 (dd, J=8.1, 4.8 Hz, 1H); 5.52 (s, 1H); 4.47 (s, 1H); 4.09 (q, J=7.3 Hz, 4H); 2.60–2.51(m, 2H); 2.16–2.08 (m, 1H); 1.41 (s, 9H); 1.26–1.13 (m, 6H) ppm. $^{13}$C-NMR (50 MHz, CDCl$_3$) δ: 171.2, 170.7, 166.2, 162.7, 155.1, 152.6, 148.5, 135.3, 127.4, 123.4, 80.3, 61.7, 61.3, 50.5, 30.6, 28.1 (3C), 26.7, 25.5, 13.9 and 13.8 ppm.

b) (2SR, 1'SR, 2'RS, 3'RS)-2-[2'-carboxy-3'-(3"-pyridylcarbonylhydrazinocarbonyl)cyclopropyl]glycine.

To a solution of ethyl (2SR, 1'SR, 2'RS, 3'RS) N-(tert-butoxycarbonyl)-2-[2'-ethoxycarbonyl-3'-(3"-pyridinecarbonylhydrazinocarbonyl)cyclopropyl]glycinate (105 mg, 0.21 mmol) in THF (2 mL) was added a solution of 0.5N LiOH (2.2 mL). The mixture was stirred for 18 h at rt. Then solvent was removed under reduced pressure and the aqueous phase was acidified with 1N HCl until pH=1. Then the mixture was evaporated under reduced pressure and a solution of HCl/AcOEt 1N (2 mL) was added. After stirring overnight, solvent was evaporated in vacuo affording the corresponding hydrochloride. The final aminoacid (40 mg, 57% yield) was isolated as zwitterion by ion exchange chromatography.

$^1$H-NMR (200 MHz, D$_2$O/Py-d5) δ: 8.63 (s, 1H); 8.38 (d, J=5.1 Hz, 1H); 7.93 (d, J=7.5 Hz, 1H); 7.28–7.21 (m, 1H); 3.86 (d, J=10.7 Hz, 1H); 2.40 (dd, J=9.1, 5.1 Hz, 1H); 2.19–2.14 (t, 1H); 2.03–1.90 (m, 1H). $^{13}$C-NMR (50 MHz, D$_2$O/Py-d5) δ: 177.4, 172.9, 170.4, 166.4, 151.9, 147.2, 136.0, 127.6, 124.1, 51.9, 28.4, 27.7, 25.9 ppm. IR (KBr): 3198, 3028, 1643, 1695, 1475, 1385, 1331, 1248, 1196, 1153, 1028, 998 and 902 cm$^{-1}$.

EXAMPLE 12

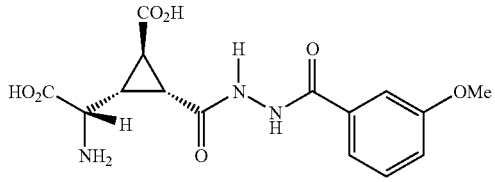

(2SR, 1'SR, 2'RS, 3'RS)-2-[2'-carboxy-3'-(3"-methoxybenzoylhydrazinocarbonyl)cyclopropyl]glycine a) Ethyl (2SR, 1'SR, 2'RS, 3'RS)N-(tert-butoxycarbonyl)-2-[2'-ethoxycarbonyl-3'-(3"-methoxybenzoylhydrazinocarbonyl) cyclopropyl]glycinate.

To a solution of ethyl (1SR, 2 SR, 5RS, 6RS) 3-tert-butoxycarbonyl-4-oxo-3-azabicyclo[3.1.0]hexane-2,6-dicarboxylate (150 mg, 0.44 mmol) in dry THF (3 mL) under argon was added 3-methoxybenzoic hydrazide (438 mg, 2.64 mmol) and potassium cyanide (1.43 mg, 0.02 mmol). After stirring overnight in an ultrasonic bath, the solvent was removed under reduced pressure. The residue was directly purified by flash chromatography (hexane/ethyl acetate 1/1) to give 206 mg of the desired compound (92% yield).

$^1$H-NMR (200 MHz, CDCl$_3$) δ: 7.38–7.20 (m, 3H); 6.99 (d, J=9.1 Hz, 1H); 5.45–5.45 (s, 1H); 4.47 (t, J=9.1 Hz, 1H); 4.13–4.01 (m, 4H); 3.75 (s, 3H); 2.62 (d, 2H); 2.08 (dd, J=10.2, 7.5 Hz, 1H); 1.40 (s, 9H); 1.16 (m, 6H) ppm.

$^{13}$C-NMR (50 MHz, CDCl$_3$) δ: 171.2, 170.7, 165.7, 163.8, 159.6, 155.0, 132.5, 129.5, 119.3, 118.4, 112.3, 80.1, 61.6, 61.1, 55.2, 50.5, 30.6, 28.1 (3C), 26.6, 25.5, 13.9, 13.7 ppm.

b) (2SR, 1'SR, 2'RS, 3'RS)-2-[2'-carboxy-3'-(3"-methoxybenzoylhydrazinocarbonyl)cyclopropyl]glycine.

To a solution of ethyl (2SR, 1'SR, 2'RS, 3'RS) N-(tert-butoxycarbonyl)-2-[2'-ethoxycarbonyl-3'-(3"-methoxybenzoylhydrazinocarbonyl)cyclopropyl]glycinate (208 mg, 0.41 mmol) in THF (3.5 mL) was added a solution of 0.5N LiOH (4 mL). The mixture was stirred for 18 h at rt. Then solvent was removed under reduced pressure and the aqueous phase was acidified with 1N HCl until pH=1 and the mixture was extracted with AcOEt. The combined organic phases were dried (MgSO$_4$) and evaporated under reduced pressure. Then, a solution of HCl/AcOEt 1N (3.2 mL) was added, and the mixture was stirred overnight. Solvent was evaporated in vacuo affording the corresponding hydrochloride. The final aminoacid (72 mg, 50% yield) was isolated as zwitterion by ion exchange chromatography.

$^1$H-NMR (200 MHz, D$_2$O/Py-d5) δ: 7.10–6.94 (m, 3H); 6.66 (d, J=8.3 Hz, 1H); 3.82 (d, J=10.5 Hz, 1H); 3.39 (s, 3H); 2.36 (dd, J=9.1, 5.1 Hz, 1H); 2.15–2.09 (t, 1H); 1.99.1.86 (m, 1H) ppm.

$^{13}$C-NMR (50 MHz, D$_2$O/Py-d5) δ: 177.4, 172.8, 170.3, 168.1, 158.6, 132.2, 129.8, 119.7, 118.3, 112.2, 55.0, 51.9, 28.3, 27.4, 25.9 ppm.

IR (KBr): 3204, 1637, 1583, 1485, 1385, 1331, 1263, 1226, 1140, 1035, 995 cm$^{-1}$.

EXAMPLE 13

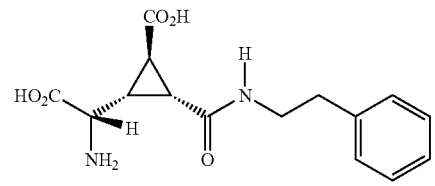

(2SR, 1'SR, 2'RS, 3'RS)-2-[2-carboxy-3'-(2"-phenylethylaminocarbonyl)cyclopropyl]glycine a) Ethyl (2SR, 1'SR, 2'RS, 3'RS)N-(tert-butoxycarbonyl)-2-[2'-ethoxycarbonyl-3'-(2"-phenylethylaminocarbonyl) cyclopropyl]glycinate.

To a solution of ethyl (1SR, 2 SR, 5RS, 6RS) 3-tert-butoxycarbonyl-4-oxo-3-azabicyclo[3.1.0]hexane-2,6-dicarboxylate (178 mg, 0.52 mmol) in dry THF (3.5 mL) under argon was added 2-phenylethylamine (0.39 mL, 3.13 mmol) and potassium cyanide (1.69 mg, 0.02 mmol). After stirring overnight in an ultrasonic bath, the solvent was removed under reduced pressure. The residue was directly purified by flash chromatography (hexane/ethyl acetate 1/1) to give 221 mg of the desired compound (91% yield).

$^1$H-NMR (200 MHz, CDCl$_3$) δ: 7.24–7.14 (m, 5H); 6.42 (t, J=5.9 Hz, 1H); 5.37 (s, 1H); 4.52 (dd, J=9.9, 8.1 Hz, 1H);

4.14–4.00 (m, 5H); 3.56–3.33 (m, 2H); 2.78 (t, J=7.3 Hz, 2H); 2.53 (t, J=5.1 Hz, 1H); 2.16 (dd, J=9.4, 5.1 Hz, 1H); 1.42 (s, 9H); 1.23–1.13 (m, 6H) ppm.

$^{13}$C-NMR (50 MHz, CDCl$_3$) δ: 171.9, 170.9, 168.0, 154.6, 138.7, 128.5, 128.4, 126.3, 79.5, 61.3, 60.9, 50.5, 41.1, 35.5, 30.2, 28.9, 28.1, 25.1, 13.9 ppm.

b) (2SR, 1'SR, 2'RS, 3'RS)-2-[2'-carboxy-3'-(2''-phenylethylaminocarbonyl)cyclopropyl]glycine.

To a solution of ethyl (2SR, 1'SR, 2'RS, 3'RS)N-(tert-butoxycarbonyl)-2-[2'-ethoxycarbonyl-3'-(2''-phenylethylaminocarbonyl)cyclopropyl]glycinate (212 mg, 0.45 mmol) in THF (4 mL) was added a solution of 0.5N LiOH (4.6 mL). The mixture was stirred for 18 h at rt. Then solvent was removed under reduced pressure and the aqueous phase was acidified with 1N HCl until pH=1 and the mixture was extracted with AcOEt. The combined organic phases were dried (MgSO$_4$) and evaporated under reduced pressure. Then, a solution of HCl/AcOEt 1N (3.6 mL) was added, and the mixture was stirred overnight. Solvent was evaporated in vacuo affording the corresponding hydrochloride. The final aminoacid (56 mg, 40% yield) was isolated as zwitterion by ion exchange chromatography.

$^1$H-NMR (200 MHz, D$_2$O/Py-d5) δ: 6.48 (m, 5H); 3.64 (d, J=9.9 Hz, 1H); 2.81 (m, 3H); 2.18–1.96 (m, 6H).

$^{13}$C-NMR (50 MHz, D$_2$O/Py-d5) δ: 177.6, 172.9, 170.6, 139.1, 128.5, 128.4, 128.3, 128.2, 125.9, 52.4, 41.0, 34.6, 28.1, 28.0, 27.5 ppm.

IR (KBr): 3258, 3063, 1637, 1560, 1388, 1238, 1190, 1030, 898 cm$^{-1}$.

EXAMPLE 14

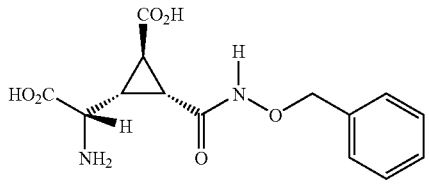

(2SR, 1'SR, 2'RS, 3'RS)-2-[2'-carboxy-3'-(benzyloxiaminocarbonyl)cyclopropyl]glycine a) Ethyl (2SR, 1'SR, 2'RS, 3'RS)N-(tert-butoxycarbonyl)-2-[2'-ethoxycarbonyl-3'-(benzyloxiaminocarbonyl)cyclopropyl]glycinate.

To a solution of ethyl (1SR, 2 SR, 5RS, 6RS) 3-tert-butoxycarbonyl-4-oxo-3-azabicyclo[3.1.0]hexane-2,6-dicarboxylate (150 mg, 0.44 mmol) in dry THF (3 mL) under argon was added O-benzylhydroxylamine hydrochloride (421.5 mg, 2.64 mmol), potassium cyanide (1.43 mg, 0.02 mmol) and triethylamine (0.36 mL, 2.64 mmol). After stirring overnight in an ultrasonic bath, the solvent was removed under reduced pressure. The residue was directly purified by flash chromatography (hexane/ethyl acetate 1.5/1) to give 182 mg of the desired compound (89% yield).

$^1$H-NMR (200 MHz, CDCl$_3$) δ: 7.41–7.34 (m, 5H); 4.91 (s, 2H); 4.48 (dd, J=9.9, 8.1 Hz, 1H); 4.22–4.07 (m, 4H); 2.64 (t, J=5.1 Hz, 1H); 2.07 (s, 1H); 1.72–1.69 (m, 1H); 1.46 (s, 9H); 1.29–1.21 (m, 6H) ppm.

$^{13}$C-NMR (50 MHz, CDCl$_3$) δ: 171.4, 170.6, 154.7, 129.1, 128.7, 128.5, 128.3, 128.2, 127.9, 77.9, 61.6, 61.1, 50.7, 30.5, 28.1, 25.9, 25.2, 13.9 ppm.

b) (2SR, 1'SR, 2'RS, 3'RS)-2-[2'-carboxy-3'-(benzyloxiaminocarbonyl)cyclopropyl]glycine.

To a solution of ethyl (2SR, 1'SR, 2'RS, 3'RS)N-(tert-butoxycarbonyl)-2-[2'-ethoxycarbonyl-3'-(benzyloxiaminocarbonyl)cyclopropyl]glycinate (168 mg, 0.36 mmol) in THF (3 mL) was added a solution of 0.5N LiOH (3.6 mL). The mixture was stirred for 18 h at rt. Then solvent was removed under reduced pressure and the aqueous phase was acidified with 1N HCl until pH=1 and the mixture was extracted with AcOEt. The combined organic phases were dried (MgSO$_4$) and evaporated under reduced pressure. Then, a solution of HCl/AcOEt 1N (3.6 mL) was added, and the mixture was stirred overnight. Solvent was evaporated in vacuo affording the corresponding hydrochloride. The final aminoacid (45 mg, 40% yield) was isolated as zwitterion by ion exchange chromatography.

$^1$H-NMR (200 MHz, D$_2$O/Py-d5) δ: 7.29–7.21 (m, 5H); 4.68 (s, 2H); 3.73 (d, J=10.5 Hz, 1H); 2.03 (d, J=8.1 Hz, 2H); 1.91–1.78 (m, 1H) ppm.

$^{13}$C-NMR (50 MHz, D$_2$O/Py-d5) δ: 177.4, 172.7, 167.9, 134.6, 129.4, 128.9, 128.5, 128.4, 78.2; 51.9, 27.6, 26.9, 24.9 ppm.

IR(KBr): 3188, 1651, 1454, 1394, 1234, 1190, 1049, 900 cm$^{-1}$.

EXAMPLE 15

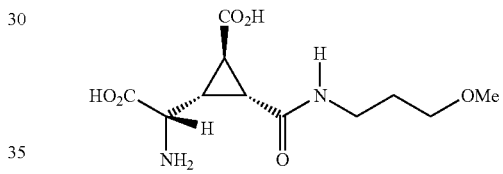

(2SR, 1'SR, 2'RS, 3'RS)-2-[2'-carboxy-3'-(3''-methoxypropylaminocarbonyl)cyclopropyl]glycine a) Ethyl (2SR, 1'SR, 2'RS, 3'RS)N-(tert-butoxycarbonyl)-2-[2'-ethoxycarbonyl-3'-(3''-methoxypropylaminocarbonyl)cyclopropyl]glycinate.

To a solution of ethyl (1SR, 2 SR, 5RS, 6RS) 3-tert-butoxycarbonyl-4-oxo-3-azabicyclo[3.1.0]hexane-2,6-dicarboxylate (181 mg, 0.53 mmol) in dry THF (3.5 mL) under argon was added 3-methoxypropylamine (0.32 mL, 3.18 mmol) and potassium cyanide (1.72 mg, 0.02 mmol). After stirring overnight in an ultrasonic bath, the solvent was removed under reduced pressure. The residue was directly purified by flash chromatography (hexane/ethyl acetate 1/1) to give 183 mg of the desired compound (80% yield).

$^1$H-NMR (200 MHz, CDCl$_3$) δ: 6.65 (s, 1H); 5.32 (s, 1H); 4.47 (dd, J=9.9, 7.8 Hz, 1H); 4.14–4.00 (m, 6H); 3.40 (t, J=5.9 Hz, 4H); 3.26 (s, 3H); 2.49 (t, J=5.4 Hz, 1H); 2.12 (dd, J=9.1, 4.8 Hz, 1H); 1.77–1.65 (m, 1H); 1.38 (s, 9H); 1.18 (t, J=7.3 Hz, 6H) ppm.

$^{13}$C-NMR (50 MHz, CDCl$_3$) δ: 171.9, 170.9, 167.7, 154.8, 79.8, 71.3, 61.2, 60.9, 58.3, 50.6, 38.1, 30.1, 28.9, 28.0, 25.0, 13.9 ppm.

b) (2SR, 1'SR, 2'RS, 3'RS)-2-[2'-carboxy-3'-(3''-methoxypropylaminocarbonyl)cyclopropyl]glycine.

To a solution of ethyl (2SR, 1'SR, 2'RS, 3'RS)N-(tert-butoxycarbonyl)-2-[2'-ethoxycarbonyl-3'-(3''-methoxypropylaminocarbonyl)cyclopropyl]glycinate (181 mg, 0.42 mmol) in THF (3 mL) was added a solution of 0.5N LiOH (4.2 mL). The mixture was stirred for 18 h at rt. Then solvent was removed under reduced pressure and the aqueous phase was acidified with 1N HCl until pH=1 and the mixture was extracted with AcOEt. The combined organic phases were dried (MgSO$_4$) and evaporated under reduced pressure. Then, a solution of HCl/AcOEt 1N (3.3 mL) was added, and the mixture was stirred overnight. Solvent was evaporated in vacuo affording the corresponding hydrochloride. The final aminoacid (57 mg, 50% yield) was isolated as zwitterion by ion exchange chromatography.

$^1$H-NMR (200 MHz, D$_2$O/Py-d5) δ: 3.80 (d, J=10.5 Hz, 1H); 3.22 (t, J=6.2 Hz, 2H); 3.09 (s, 3H); 3.02 (t, J=7.3 Hz, 2H); 2.16 (dd, J=9.1, 5.1 Hz, 1H); 2.06 (t, J=5.6 Hz, 1H); 1.85 (dt, J=6.2, 9.7 Hz, 1H); 1.55 (qui, J=6.7 Hz, 2H) ppm.

$^{13}$C-NMR (50 MHz, D$_2$O/Py-d5) δ: 178.0, 173.0, 170.5, 69.7, 57.6, 52.1, 36.4, 28.1, 27.9, 27.8, 27.1 ppm.

IR (KBr): 3086, 2939, 1643, 1564, 1450, 1387, 1246, 1192, 1113, 1030 and 968.4 cm$^{-1}$.

EXAMPLE 16

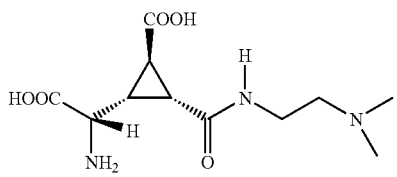

(2SR, 1'SR, 2'RS, 3'RS)-2-[2'-carboxy-3'-(2''-dimethylaminoethylaminocarbonyl)cyclopropyl]glycine a) Ethyl (2SR, 1'SR, 2'RS, 3'RS) N-(tert-butoxycarbonyl)-2-[2'-ethoxycarbonyl-3'-(2''-dimethylaminoethylaminocarbonyl) cyclopropyl]glycinate.

To a solution of ethyl (1SR, 2 SR, 5RS, 6RS) 3-tert-butoxycarbonyl-4-oxo-3-azabicyclo[3.1.0]hexane-2,6-dicarboxylate (189 mg, 0.55 mmol) in dry THF (3.5 mL) under argon was added N,N-dimethylethylenediamine (0.36 mL, 3.32 mmol) and potassium cyanide (1.76 mg, 0.02 mmol). After stirring overnight in an ultrasonic bath, the solvent was removed under reduced pressure. The residue was directly purified by flash chromatography (hexane/ethyl acetate 2/1) to give 200 mg of the desired compound (84% yield).

$^1$H-NMR (200 MHz, CDCl$_3$) δ: 6.65 (s, 1H); 5.33 (s, 1H); 4.53 (dd, J=9.9, 8.1 Hz, 1H); 4.09 (qui, J=7.5 Hz, 5H); 3.44–3.18 (m, 3H); 2.51 (t, 1H); 2.39 (t, J=5.9 Hz, 1H); 2.19 (s, 6H); 1.40 (s, 9H); 1.20 (t, J=7.0 Hz, 6H) ppm.

$^{13}$C-NMR (50 MHz, CDCl$_3$) δ: 171.8, 170.9, 167.9, 154.8, 80.0, 61.3, 61.0, 57.5, 50.6, 44.9, 37.0, 30.3, 28.9, 28.1, 25.2, 14.3, 14.0 ppm.

b) (2SR, 1'SR, 2'RS, 3'RS)-2-[2'-carboxy-3'-(2''-dimethylaminoethylaminocarbonyl)cyclopropyl]glycine.

To a solution of ethyl (2SR, 1'SR, 2'RS, 3'RS)N-(tert-butoxycarbonyl)-2-[2'-ethoxycarbonyl-3'-(2''-dimethylaminoethylaminocarbonyl)cyclopropyl]glycinate (200 mg, 0.46 mmol) in THF (3 mL) was added a solution of 0.5N LiOH (4.6 mL). The mixture was stirred for 18 h at rt. Then solvent was removed under reduced pressure and the aqueous phase was acidified with 1N HCl until pH=1. The mixture was evaporated under reduced pressure affording the corresponding hydrochloride. The final aminoacid (70 mg, 55% yield) was isolated as zwitterion by ion exchange chromatography.

$^1$H-NMR (200 MHz, D$_2$O/Py-d5) δ: 3.60 (d, J=11.0 Hz, 1H); 3.54–3.45 (m, 1H); 3.38–3.21 (m, 1H); 3.09–2.98 (m, 2H); 2.61 (s, 6H); 2.10–1.96 (m, 2H); 1.81–1.68 (m, 1H) ppm.

$^{13}$C-NMR (50 MHz, D$_2$O/Py-d5) δ: 177.4, 172.9, 171.5, 57.0, 52.2, 42.9, 34.2, 28.0, 27.3, 27.1 ppm.

IR (KBr): 3422, 3051, 1641, 1572, 1379, 1244, 1169, 1097, 1026 and 964 cm$^{-1}$.

EXAMPLE 17

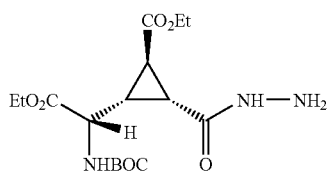

Ethyl (2SR, 1'SR, 2'RS, 3'RS)N-(tert-butoxycarbonyl)-2-[2'-ethoxycarbonyl-3'-hydrazinocarbonylcyclopropyl]glycinate To a solution of ethyl (1SR, 2 SR, 5RS, 6RS) 3-tert-butoxycarbonyl-4-oxo-3-azabicyclo[3.1.0]hexane-2,6-dicarboxylate (195 mg, 0.57 mmol) in dry THF (3.8 mL) under argon was added hydrazine (0.1 mL, 3.43 mmol) and potassium cyanide (1.86 mg, 0.02 mmol). After stirring overnight in an ultrasonic bath, the solvent was removed under reduced pressure. The residue was directly purified by flash chromatography (ethyl acetate) to give 55 mg of the desired compound (26% yield).

$^1$H-NMR (200 MHz, CDCl$_3$) δ: 5.40 (d, J=8.1 Hz, 1H); 4.50 (dd, J=9.9, 7.8 Hz, 1H); 4.19–4.03 (m, 4H); 2.59 (t, J=5.4 Hz, 1H); 2.19 (dd, J=9.4, 5.1 Hz, 1H); 2.06–2.04 (m, 1H); 1.43 (s, 9H); 1.22 (t, J=7.0 Hz, 6H) ppm.

$^{13}$C-NMR (50 MHz, CDCl$_3$) δ: 171.6, 170.9, 169.2, 155.0, 79.8, 61.5, 61.1, 50.5, 30.2, 28.1, 26.9, 25.1, 14.0, 13.9 ppm.

EXAMPLE 18

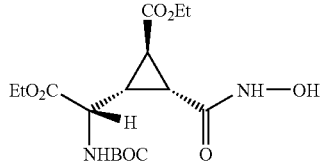

Ethyl (2SR, 1'SR, 2'RS, 3'RS) N-(tert-butoxycarbonyl)-2-[2'-ethoxycarbonyl-3'-hydroxyaminocarbonylcyclopropyl]glycinate To a solution of ethyl (1SR, 2 SR, 5RS, 6RS) 3-tert-butoxycarbonyl-4-oxo-3-azabicyclo[3.1.0]hexane-2,6-dicarboxylate (65 mg, 0.19 mmol) in dry THF (1.2 mL) under argon was added hydroxylamine hydrochloride (79.2 mg, 1.14 mmol), potassium cyanide (0.61 mg, 0.01 mmol) and triethylamine 0.15 mL (1.14 mmol). After stirring overnight in an ultrasonic bath, the solvent was removed under reduced pressure. The residue was directly purified by flash chromatography (hexane/ethyl acetate 1:1) to give 55 mg of the desired compound (77% yield).

$^1$H-NMR (200 MHz, CDCl$_3$) δ: 5.40 (s, 1H); 4.50, (m, 1H); 4.14 (m, 4H); 2.59 (t, 3H); 2.32 (dd, 1H); 2.22 (m, 1H); 1.43 (s, 9H); 1.23 (t, 3H) ppm.

$^{13}$C-NMR (50 MHz, CDCl$_3$) δ: 171.6, 171.0, 166.8, 155.4, 80.4; 61.9; 61.3; 50.6; 30.2; 28.2; 25.9; 25.0; 14.0; 13.8 ppm.

EXAMPLE 19

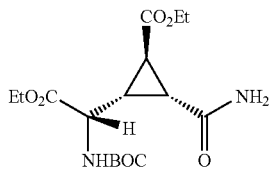

Ethyl (2SR, 1'SR, 2'RS, 3'RS)N-(tert-butoxycarbonyl)-2-[2'-ethoxycarbonyl-3'-(aminocarbonyl)cyclopropyl]glycinate To a solution of ethyl (1SR, 2 SR, 5RS, 6RS) 3-tert-butoxycarbonyl-4-oxo-3-azabicyclo[3.1.0]hexane-2,6-dicarboxylate (200 mg, 0.58 mmol) in dry CH$_2$Cl$_2$ (3 mL), NH$_3$(g) was bubble for 15 min. Then AlMe$_3$ (0.88° mmol) was added, and the mixture was stirred for 20 h at r.t. The mixture was quenched with HCl 0.1N at 0° C. and stirred for 15 min. The white solid formed was filtered, and the liquids concentrated in vacuo. The residue was purified by flash chromatography (hexane/ethyl acetate 2/1) to give 114 mg of the desired compound (54% yield).

$^1$H-NMR (200 MHz, CDCl$_3$) δ: 6.15 (bs, 2H); 5.25 (bs, 1H); 4.53 (dd, 1H); 4.12 (dc, 4H); 2.55 (t, 1H); 2.26 (dd, 1H) 2.04 (m, 1H), 1.43(s, 9H) and 1.24 (dt, 6H) ppm.

$^{13}$C-NMR (50 MHz, CDCl$_3$) δ: 171.8; 171.1; 170.7; 155.1; 80.0; 61.6; 61.4; 50.3 30.5; 28.3; 28.1 (3C); 25.5 and 14.0 (2C) ppm.

EXAMPLE 20

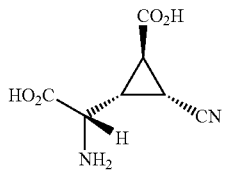

(2SR, 1'SR, 2'RS, 3'RS)-2–12'-carboxy-3-cyanocyclopropyl]glycine a) Ethyl (2SR, 1'SR, 2'RS, 3'RS)N-(tert-butoxycarbonyl)-2-[2'-ethoxycarbonyl-3'-cyanocyclopropyl]glycinate.

To a solution of ethyl (2SR, 1'SR, 2'RS, 3'RS)N-(tert-butoxycarbonyl)-2-[2'-ethoxycarbonyl-3'-(aminocarbonyl)cyclopropyl]glycinate (223 mg, 0.62 mmol) in dry THF (4 mL), pyridine (0.17 mL, 2.48 mmol) was added. Then, trifluoroacetic anhydride (0.11 mL, 1.48 mmol) was added dropwise and the mixture was stirred at room temperature for 19 hours. The reaction was quenched with water and extracted with CH$_2$Cl$_2$. The residue was purified by flash chromatography using AcOEt/hexane (1:1) as eluent to give the desired compound (79% yield).

$^1$H-NMR (200 MHz, CDCl$_3$) δ: 5.28 (bd, 1H); 4.34–4.11 (dq, 5H); 2.60 (m, 1H); 2.23–2.16 (dd, 1H); 2.06–1.94 (m, 1H); 1.45 (s, 9H) and 1.37–1.21 (dt, 6H) ppm.

$^{13}$C-NMR (50 MHz, CDCl$_3$) δ: 169.5; 169.4; 116.5; 80.6; 62.4; 61.9; 53.0; 30.8; 28.8; 28.1; 25.4; 13.9 ppm.

b) (2SR, 1'SR, 2'RS, 3'RS)-2-[2'-carboxy-3-cyanocyclopropyl]glycine.

To a solution of the correspondent ethyl (2SR, 1'SR, 2'RS, 3'RS)N-(tert-butoxycarbonyl)-2-[2'-ethoxycarbonyl-3'-cyanocyclopropyl]glycinate (50 mg, 0.14 mmol) in THF (2 mL) was added a solution of 0.25N LiOH (0.56 mmol). The mixture was stirred at rt for 48 h. Then solvent was removed under reduced pressure and the aqueous phase was acidified with 1N HCl until pH=1 and the mixture was extracted with Et2O. The combined organic phases were dried (MgSO$_4$) and evaporated under reduced pressure. Then, a solution of HCl/AcOEt 1N was added, and the mixture was stirred overnight. Solvent was evaporated in vacuo affording the corresponding hydrochloride. The final aminoacid (10 mg, 40%) was isolated as zwitterion by ion exchange chromatography.

$^1$H-NMR (200 MHz, D$_2$O/Py-d5) δ: 3.65 (d, 1H,); 2.73 (d, 1H) and 2.41–2.22 (m, 2H) ppm.

$^{13}$C-NMR (50 MHz, D$_2$O/Py-d5) δ: 174.6; 171.2; 118.5; 54.8; 28.5; 27.2 and 25.1 ppm.

IR (KBr): 3414, 2924, 2855, 1703, 1693, 1631, 1390, 1275, 1095 and 900 cm$^{-1}$.

EXAMPLE 21

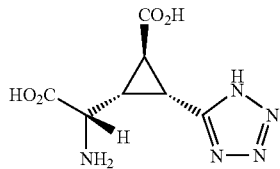

(2SR, 1'SR, 2'RS, 3'RS)-2-[2'-carboxy-3-(tetrazol-5'-yl)cyclopropyl]glycine

A mixture of ethyl (2SR, 1'SR, 2'RS, 3'RS)N-(tert-butoxycarbonyl)-2-[2'-ethoxycarbonyl-3'-cyanocyclopropyl]glycinate (95 mg, 0.27 mmol) and Bu3SnN3 (0.22 mL, 0.81 mol) was stirred at 90$^2$C for 24 h. Then HCl 1N was added and stirred under reflux for 18 h. Water was added, and the solulution was washed with ethyl ether. The aqueous phase was concentrated in vacuo, and the final aminoacid (50 mg, 79% yield) was isolated as zwitterion by ion exchange chromatography.

$^1$H-NMR (200 MHz, D$_2$O/Py-d5) δ: 3.65 (d, 1H, J=10.5 Hz); 2.28 (s, 3H) and 1.97–1.62 (m, 1H) and 1.75–1.62 (m, 1H) ppm $^{13}$C-NMR (50 MHz, D$_2$O/Py-d5) δ: 177.2; 171.6; 157.9; 52.2; 27.8; 26.9; 20.0 ppm.

IR (KBr): 3426, 3057, 2926, 1711, 1631, 1390, 1232, 1032 and 929 cm$^{-1}$.

The invention claimed is:

1. A compound of the formula:

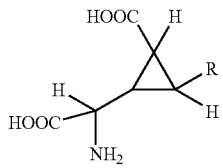

I in which:

R represents CN or a group of formula CONR$^1$(X$^1$R$^2$);

X$^1$ represents a bond, NHCO, NH, O or (CH$_2$)$_p$—Y— in which Y represents O, S, NR$^b$, or COO and p is 2 or 3, and R$^1$, R$^2$ and R$^b$ each independently represents hydrogen; C$_{1-10}$ alkyl; C$_{2-10}$ alkenyl; C$_{2-10}$ alkynyl; aryl; aryl-C$_{1-10}$ alkyl; aryl -C$_{2-10}$ alkenyl; aryl-C$_{2-10}$ alkynyl; heteroaryl; C$_{3-8}$ cycloalkyl; C$_{3-8}$-cycloalkyl-C$_{1-10}$ alkyl; a group of formula CH(R$^3$)COOH in which R$^3$ represents an amino acid residue; or R$^1$ and X$^1$R$^2$ together with the nitrogen atom to which they are attached form a 5 to 6-membered saturated heterocyclic ring, which ring may optionally be fused with an aromatic ring;

an ester thereof;

or a salt of said compound of formula I or said ester thereof.

2. A compound of formula I, a pharmaceutically acceptable metabolically labile ester thereof or a pharmaceutically acceptable salt of said compound of formula I or said pharmaceutically acceptable metabolically labile ester thereof, as claimed in claim 1.

3. A compound as claimed in claim 1 or claim 2, which has the configuration

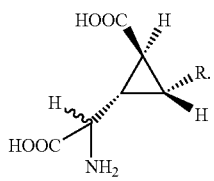

4. A compound as claimed in claim 3, which has the configuration

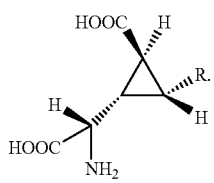

5. A compound according to any one of claims 1 or 2 in which R$^1$ is hydrogen or methyl.

6. A compound as claimed in claim 5, in which R$^1$ is hydrogen.

7. A compound as claimed in any one of claims 1 or 2 in which R$^2$X$^1$ is hydrogen; methyl; phenyl; benzyl; cyclohexyl; cyclohexylmethyl; HOOCCH$_2$; phenylCONH or, together with R$^1$ and the nitrogen to which they are attached, morpholinyl and tetrahydroisoquinolinyl.

8. A compound as claimed in claim 1 which is selected from:

(2SR, 1'SR, 2'RS, 3'RS)-2-[2'-carboxy-3'-(phenylmethylaminocarbonyl)cyclopropyl]glycine;

(2SR, 1'SR, 2'RS, 3'RS)-2-[2'-carboxy-3'-(methylaminocarbonyl)cyclopropyl]glycine;

(2SR, 1'SR, 2'RS, 3'RS)-2-[2'-carboxy-3'-(cyclohexylmethylaminocarbonyl)cyclopropyl]glycine;

(2SR, 1'SR, 2'RS, 3'RS)-2-[3'-(benzoylhydrazinocarbonyl)-2'-carboxycyclopropyl]glycine;

(2SR, 1'SR, 2'RS, 3'RS)-2-[2'-carboxy-3'-(carboxymethylaminocarbonyl)cyclopropyl]glycine;

(2SR, 1'SR, 2'RS, 3'RS)-2-[2'-carboxy-3'-(phenylaminocarbonyl)cyclopropyl]glycine;

(2SR, 1'SR, 2'RS, 3'RS)-2-[2'-carboxy-3'-(dimethylaminocarbonyl)cyclopropyl]glycine;

(2SR, 1'SR, 2'RS, 3'RS)-2-[2'-carboxy-3'-(morpholinylcarbonyl)cyclopropyl]glycine;

(2SR, 1'SR, 2'RS, 3'RS)-2-[2'-carboxy-3'-(tetrahydroisoquinolylcarbonyl)cyclopropyl]glycine;

(2SR, 1'SR, 2'RS, 3'RS)-2-[2'-carboxy-3'-(phenylhydrazinocarbonyl)cyclopropyl]glycine hydrochloride;

(2SR, 1'SR, 2'RS, 3'RS)-2-[2'-carboxy-3'-(3"-pyridylcarbonylhydrazinocarbonyl)cyclopropyl]glycine;

(2SR, 1'SR, 2'RS, 3'RS)-2-[2'-carboxy-3'-(3"-methoxybenzoylhydrazinocarbonyl)cyclopropyl]glycine;

(2SR, 1'SR, 2'RS, 3'RS)-2-[2'-carboxy-3'-(2"-phenylethylaminocarbonyl)cyclopropyl]glycine; and (2SR, 1'SR, 2'RS, 3'RS)-2-[2'-carboxy-3'-(benzyloxiaminocarbonyl)cyclopropyl]glycine; and (2SR, 1'SR, 2'RS, 3'RS)-2-[2'-carboxy-3'-(3"-methoxypropylaminocarbonyl)cyclopropyl]glycine;

(2SR, 1'SR, 2'RS, 3'RS)-2-[2'-carboxy-3'-(2"-dimethylaminoethylaminocarbonyl)cyclopropyl]glycine;

(2SR, 1'SR, 2'RS, 3'RS)-2-[2'-carboxy-3'-cyanocyclopropyl]glycine; and cyclopropyl]glycine;

and salts and esters thereof.

9. A process for preparing a compound as claimed in any one of claims 1, 2 or 8, which comprises:

(a) deprotecting a compound of formula

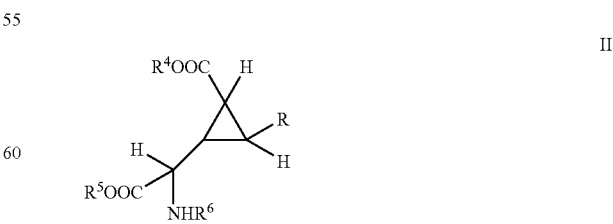

II in which R$^4$ and R$^5$ each independently represents hydrogen or a carboxyl protecting group, and R$^6$ represents hydrogen or an amine protecting group;

(b) hydrolysing a compound of formula

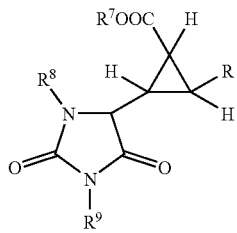

III in which $R^7$ represents a hydrogen atom or a carboxyl protecting group, and $R^8$ and $R^9$ each independently represents a hydrogen atom; a $C_{1-4}$ alkyl group or a phenyl $C_{1-4}$ alkyl group in which the phenyl group is unsubstituted or substituted by halo, $C_{1-4}$ alkyl, $C_{1-4}$ alkoxy or $C_{3-4}$ alkenyl; or (c) hydrolysing a compound of formula

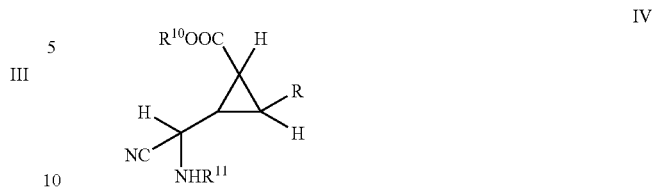

IV in which $R^{10}$ represents a hydrogen atom or a carboxy protecting group, and $R^{11}$ represents a hydrogen atom or an amine protecting group;

followed when necessary by recovering a diastereomer or isomer of the compound, or forming an ester thereof or a salt of said compound of formula I or said ester thereof.

10. A pharmaceutical formulation comprising a compound as claimed in any one of claims 2 or 8 together with a pharmaceutically acceptable carrier, diluent or excipient.

* * * * *